(12) United States Patent
Kume et al.

(10) Patent No.: US 8,413,482 B2
(45) Date of Patent: *Apr. 9, 2013

(54) SENSOR

(75) Inventors: Makoto Kume, Inuyama (JP); Noboru Matsui, Iwakura (JP)

(73) Assignee: NGK Spark Plug Co., Ltd., AIchi (JP)

( * ) Notice: Subject to any disclaimer, the term of this patent is extended or adjusted under 35 U.S.C. 154(b) by 497 days.

This patent is subject to a terminal disclaimer.

(21) Appl. No.: 12/635,020

(22) Filed: Dec. 10, 2009

(65) Prior Publication Data

US 2010/0139364 A1   Jun. 10, 2010

(30) Foreign Application Priority Data

Dec. 10, 2008  (JP) .................................. 2008-313928
Mar. 19, 2009  (JP) .................................. 2009-068460

(51) Int. Cl.
*G01N 7/00* (2006.01)

(52) U.S. Cl. ....................................................... 73/23.2

(58) Field of Classification Search ..................... 73/23.2
See application file for complete search history.

(56) References Cited

U.S. PATENT DOCUMENTS 6,688,157 B2 *   2/2004   Yamada et al. ................ 73/23.2
8,191,414 B2 *   6/2012   Kume et al. ................ 73/114.73
2008/0099334 A1   5/2008   Yamauchi

FOREIGN PATENT DOCUMENTS

| JP | 1-071662 U | 5/1989 |
| JP | 2005-091289 A | 4/2005 |
| JP | 2007-047093 A | 2/2007 |
| JP | 2008-111712 A | 5/2008 |
| JP | 2009-047574 A | 3/2009 |

\* cited by examiner

*Primary Examiner* — Hezron E Williams
*Assistant Examiner* — Rodney T Frank
(74) *Attorney, Agent, or Firm* — Sughrue Mion, PLLC

(57) ABSTRACT

A sensor including: a sensor element; terminal metal fittings; a terminal surrounding member; and lead wires. The terminal surrounding member is divided into a front side surrounding member and a rear side surrounding member, and a rear end face of the front side surrounding member abuts a front end face of the rear side surrounding member. The sensor includes a fitting structure including a recess portion formed on one of the rear and front end faces and a protruding portion formed on the other, such that one of the front side surrounding member and the rear side surrounding member is prevented from rotating relative to the other about an axis of the sensor, and is prevented from deviating in a direction perpendicular to the axis of the sensor relative to the other.

6 Claims, 17 Drawing Sheets

SENSOR

BACKGROUND OF THE INVENTION

1. Field of the Invention

The present invention relates to a sensor, and more particularly to a gas sensor including an oxygen sensor, an NOx sensor and an HC sensor for detecting the concentration of a specific gas component in an exhaust gas discharged, from an internal combustion chamber, or a temperature sensor for detecting the temperature of an exhaust gas.

2. Description of the Related Art

Sensors are generally used for controlling the air-fuel ratio of a motor vehicle engine, and include a sensor element having electrical properties which change in accordance with the concentration of a specific gas component in the engine exhaust gas (e.g., JP-A-2007-47093). FIG. 18 shows such a gas sensor (hereinafter, also referred to as a sensor) 1. For example, the gas sensor 1 includes a sensor element (hereinafter also referred to as an element) 21 made of a solid electrolyte having oxygen ion conduction properties, a metal shell (a shell main body) 11 for holding the sensor element 21, and a metallic protective sleeve (an outer sleeve) 81 provided on a rear end (an upper end in the figures) side of the metal shell 11. A terminal surrounding member (also referred to as a separator) 70 is disposed within the protective sleeve 81. As used herein, a "rear end" denotes an upper end of the sensor or components thereof, and a "front end" denotes an opposite end (a lower end) thereof.

In the sensor 1 configured as described above, the terminal surrounding member 70 is made of an electrically insulating material such as a ceramic. As shown in FIG. 18, the terminal surrounding member 70 has terminal holes (hereinafter, also referred to as holes) 75 extending straight in a front-rear direction. Terminal metal fittings 51 are positioned and accommodated in the holes 75, and the holes 75 are partitioned so as to ensure electrical insulation not only between an inner surface of the protective sleeve 81 and the terminal metal fittings 51 but also between the terminal metal fittings 51 (see FIG. 19). Each of the terminal metal fittings 51 includes a terminal connecting portion 53 as a plate spring disposed at a front end of the terminal metal fitting 51. The terminal connecting portions 53 are pressed against respective electrode terminals 25 in the holes 75 by the spring characteristic of the terminal connecting portion 53. The electrode terminals 25 are provided on side surfaces 24 of the element 21 positioned at a center of the terminal surrounding member 70. Accordingly, the terminal metal fittings 51 are electrically connected to respective electrode terminals 25. The terminal metal fittings 51 are connected to front ends (core wire portions) of lead wires 61 by crimping clamp portions (barrels) 57 which extend from the terminal connecting portions 53 by way of relay wire portion 55 to thereby be positioned at the rear ends thereof. The individual lead wires 61 are passed through a sealing elastic member 101 disposed within the protective sleeve 81 and pulled outside the sensor.

In the sensor 1, the sensor element 21 has a long flat plate-like (strip-like) shape. Also, for example, three electrode terminals 25 are provided side by side on one of opposing side surfaces (two facing main plate surfaces) 24, 24 of a portion of the sensor element 21 which lies near its rear end or a rear portion thereof. In the same figure, two terminal electrodes 25 are provided side by side on the other (opposite) side surface 24. On the other hand, the individual terminal metal fittings 51 are disposed within the holes 75 which are formed side by side and partitioned in the terminal surrounding member 70 so as to correspond to the electrode terminals 25, and the terminal connecting portions 53 are pressed against corresponding electrode terminals 25 on the element 21 so as to make electrical connections by virtue of their spring characteristics (see FIG. 18). In this sensor 1, the clamping portion 57 of each terminal metal fitting 51 clamps the front end of the lead wire by a crimping piece 58 that is bent towards the element 21 (an axis G in FIG. 18).

As described above, in the sensor 1, the terminal metal fittings 51 are disposed in the holes 75 which are formed side by side in the terminal surrounding member 70 (see FIG. 19). Consequently, the lead wires 61, which are connected to respective clamping portions 57 at the rear ends of the terminal metal fittings 51, are led out so as to extend in the rear direction in a similar side-by-side arrangement to that of the clamping portions 57. Because of this, the through holes 105 in the sealing elastic member 101, through which the lead wires 61 are passed, open in an arrangement corresponding to the arrangement of the holes 75 shown in FIG. 19 when viewed from the direction of the axis G (a rear end of the sensor).

On the other hand, the sealing elastic member 101 is disposed within the sealing sleeve portion 83 positioned at a rear portion of the protective sleeve 81. In order to ensure a good seal, the sealing sleeve portion 83 is crimped so as to be reduced in diameter from an outer circumferential surface thereof. The sealing elastic member 101 ensures sealing within the through holes 105 through which the individual lead wires 61 are inserted by radial compression resulting from the crimping. In the sealing structure of the lead wires 61, the lead wires 61 which are passed through the through holes 105 are preferably compressed equally and effectively. To obtain this result, and based on the fact that the sealing elastic member 101 normally has a circular cross section (a shape when viewed from a rear end side of the sensor), the through holes 105, as shown in FIG. 20, are preferably disposed at equal angular intervals or an interval close thereto on a circumference (an imaginary circumference) which is concentric with the circular shape.

Consequently, as with the sensor 1 shown in FIG. 18 in which three electrode terminals 25 are provided side by side on the one side surface of the element 21, the clamping portion 57 at the rear end of the terminal metal fitting 51 that is connected to a center electrode terminal 25 is preferably provided further to the outside in FIG. 18 (further rightwards in the figure) than the clamping portions 57 at the rear ends of the terminal metal fittings 51 positioned on both sides of the center terminal metal fitting 51. Namely, the clamping portions 57 are preferably arranged in a manner similar to the through holes 105 in the sealing elastic member 101. On the other hand, to secure this arrangement with respect to the center terminal metal fitting 51, the rear end of the clamping portion 57 is eccentrically offset outwards by bending the relay wire portion 55 residing between the terminal connecting portion 53 and the clamping portion 57 into a crank-like shape or by orienting outwards a crimping portion 58 constituting the clamping portion 57.

3. Problems to be Solved by the Invention

When attempting to eccentrically offset the clamping portion 57 at the rear end in an outwards direction, however, a rear portion of the hole 75 formed in the terminal surrounding member 70 in which the center terminal metal fitting 51 is disposed must be bent outwards into a crank-like shape relative to a rear portion so as to match the shape of the terminal metal fitting. This requires the straight hole structure to be modified into a complex structure. When attempting to obtain such a complex structure, however, an interior structure of the terminal surrounding member 70 is also made complex.

To alleviate this problem, one configuration has been proposed in which the terminal surrounding member 70 is divided in a front-rear direction into a front side surrounding member and a rear side surrounding member, and a rear end face of the front side surrounding member abuts a front end face of the rear side surrounding member. When the one terminal surrounding member is made by combining together the two members in the manner described above, since the degree of freedom in designing the structure of the holes therein and the shape and structure of the terminal metal fittings disposed in the holes is enhanced, the aforesaid problem can be solved. Namely, even when the holes are formed so as to extend in a straight line in parallel with the axis, holes provided in the rear side surrounding member may only have to be provided so as to be eccentrically offset outwards to an appropriate degree relative to the holes provided in the front side surrounding member. Moreover, when such a two-part structure is adopted, part of the terminal metal fitting, for example, can be held at an abutting portion between the two separate surrounding portions, thereby making it possible to obtain an advantage of preventing the terminal metal fitting whose part is so held from moving in the front-rear direction.

However, the configuration in which the single terminal surrounding member is made up of the two divided terminal surrounding members involves the following demerit. The terminal surrounding member is made by combining the two members, and therefore, when considering that the sensor is subjected to various types of vibration due to being mounted in a motor vehicle for use, the position of the sensor tends to be unstable when the sensor is disposed within the protective sleeve 81. Namely, when the two-part structure is adopted, there is a risk that the rear side surrounding member moves so as to rotate about an axis thereof relative to the front side surrounding member, or that both the surrounding members move in a lateral direction relative to each other in such a way that the centers of both the surrounding members deviate from each other. Then, when such movement occurs, the terminal metal fittings disposed in the interiors thereof also move accordingly, leading to likely deformation of the terminal metal fittings. In addition, such structure is prone to an electrical connection failure between the terminal metal fittings and the electrode terminals on the element, leading to reduced reliability.

SUMMARY OF THE INVENTION

The invention was made in view of the above circumstances, and an object thereof is to provide a sensor capable of enhancing the degree of freedom in designing the structure of holes provided in a terminal surrounding member, and the shape and structure of terminal metal fittings disposed within the holes, by adopting a two-part structure of the terminal surrounding member in which the terminal surrounding member is divided into two terminal surrounding members in the front-rear direction. Another object thereof is to provide a sensor capable of maintaining a reliable electrical connection between electrode terminals of an element disposed within the terminal surrounding member and the terminal metal fittings. This is achieved by preventing one of the divided terminal surrounding members from rotating on an axis thereof relative to the other and further, by preventing one of the divided terminal surrounding members from moving relative to the other so that their respective axes do not deviate in a lateral direction even when a two-part structure is adopted.

In a first aspect, the above objects of the invention have been achieved by providing a sensor extending in a front-rear direction from a front end thereof to a rear end thereof, the sensor comprising: a sensor element extending in the front-rear direction and comprising a plurality of electrode terminals; a plurality of terminal metal fittings pressed against and connected to respective electrode terminals of the sensor element; a terminal surrounding member made of an insulating material and having terminal holes in which the respective metal terminal elements extend in the front-rear direction, so as to surround the plurality of terminal metal fittings; and a plurality of lead wires connected to the respective terminal metal fittings and which are led out from the rear end of the sensor to an outside thereof, wherein the terminal surrounding member is divided into a front side surrounding member and a rear side surrounding member in the front-rear direction, and a rear end face of the front side surrounding member abuts a front end face of the rear side surrounding member, and wherein the sensor comprises a fitting structure comprising a recess portion formed on one of the rear end face and the front end face and a protruding portion formed on the other of the rear end face and the front end face and fitted in the recess portion, in a state in which the rear end face of the front side surrounding member and the front end face of the rear side surrounding member abut each other, so as to prevent one of the front side surrounding member and the rear side surrounding member from rotating relative to the other of the front side surrounding member and the rear side surrounding member about an axis of the sensor, and so as to prevent one of the front side surrounding member and the rear side surrounding member from deviating in a direction perpendicular to the axis of the sensor relative to the other.

In a second aspect, the invention provides a sensor according to the first aspect, wherein one or more recess portions recessed towards a front end side or one or more protruding portions protruding towards a rear end side are formed on the rear end face of the front side surrounding member, and one or more protruding portions protruding towards the front end side or one or more recess portions recessed towards the rear end side are formed on the front end face of the rear side surrounding member.

In a third aspect, the invention provides a sensor according to the second aspect, wherein a plurality of recess portions recessed towards the front end side or a plurality of protruding portions protruding towards the rear end side are formed on the rear end face of the front side surrounding member, and a plurality of protruding portions protruding towards the front end side or a plurality of recess portions recessed towards the rear end side are formed on the front end face of the rear side surrounding member.

In a fourth aspect, the invention provides a sensor according to the third aspect, wherein the protruding portions and the recess portions are formed so as to be exposed on an outer circumferential surface of the front side surrounding member and the rear side surrounding member.

In a fifth aspect, the invention provides a sensor according to the second aspect, wherein one recess portion recessed towards the front end side or one protruding portion protruding towards the rear end side is formed on the rear end face of the front side surrounding member, and one protruding portion protruding towards the front end side or one recess portion recessed towards the rear end side is formed on the front end face of the rear side surrounding member, wherein the protruding portion and the recess portion are formed so as to be exposed on an outer circumferential surface of the front side surrounding member and the rear side surrounding member, and wherein the protruding portion and the recess portion have a shape that narrows from an outer circumferential side of the front side surrounding member and the rear side surrounding member towards a center side of the front side surrounding member and the rear side surrounding member.

In a sixth aspect, the invention provides a sensor according to the second aspect, wherein one recess portion recessed towards the front end side or one protruding portion protruding towards the rear end side is formed on the rear end face of the front side surrounding member, and one protruding portion protruding towards the front end side or one recess portion recessed towards the rear end side is formed on the front end face of the rear side surrounding member, wherein the protruding portion and the recess portion are formed so as not to be exposed on an outer circumferential surface of the front side surrounding member and the rear side surrounding member, and wherein the protruding portion and the recess portion have an elliptical or polygonal shape when viewed in the front-rear direction.

In the sensor of the invention configured as described above, the terminal surrounding member has a two-part structure in which the rear end face of the front side surrounding member (hereinafter, also referred to as the rear end face) and the front end face of the rear side surrounding member (hereinafter, also referred to as the front end face) abut, and additionally, the terminal surrounding member adopts the fitting structure described above. Such structure prevents the surrounding members from rotating relative to one another about their axes, and moreover, prevents both of the surrounding members from deviating in a lateral direction relative to one another. Further, not only can this configuration reduce deformation of the terminal metal fittings disposed in the interior of the terminal surrounding member, this configuration can also enhance the reliability of electrical connection of the terminal metal fittings with the electrode terminals on the element and reduce contact failure therebetween.

Namely, in the sensor of the invention, since the deformation of the terminal metal fittings is prevented and the reliability of electrical connection between the electrode terminals on the element and the terminal metal fittings is maintained by adopting the two-part structure in which the terminal surrounding member is divided into the two surrounding members, the degree of freedom in designing the shape and structure of the terminal surrounding member itself and the holes formed therein as well as the shape and structure of the terminal metal fittings which are disposed in the holes can be enhanced.

When the one recess portion is provided on either of the front end face and the rear end face and the one protruding portion is provided on the other (for example, the one recess portion is provided on the front end face and the one protruding portion is provided on the rear end) such that the recess portion and the protruding portion have a specific structure and are fitted on and in each other, such structure can prevent the two surrounding members from rotating about their own axes relative to each other, and can prevent the two surrounding members from deviating in the lateral direction relative to each other. Further, specific shapes are selected for the recess portion and the protruding portion. For example, assuming that the recess portion is formed on the front side surrounding member, when the recess portion is not exposed to an outer circumferential surface of the front side surrounding member when the front side surrounding member is seen from a rear end side thereof, an elliptical or polygonal shape is selected. In the event that the recess portion is formed into being exposed to a portion of an outer circumferential surface of the front side surrounding member, a shape is selected in which that portion of the recess which lies on an outer circumferential surface side is narrower than a portion lying on a center side (for example, an elliptical, trapezoidal or fan-like shape).

However, when the plurality of recess portions are formed on either of the front end face and the rear end face and the plurality of protruding portions are formed on the other and when the recess portions and the protruding portions are fitted in and on to each other exactly, such structure can prevent both of the surrounding members from rotating relative to each other on their own axes and from moving in the lateral direction relative to each other without specifying shapes for the recess portions and the protruding portions. Further, the terminal surrounding member can be easily fabricated, without affecting the arrangement of the holes through which the terminal metal fittings are inserted, by forming a recess portion exposed to an outer circumferential surface of the front side surrounding member or by providing a protruding portion which protrudes in a rising fashion on the rear end face, and by forming on the front end face a protruding portion or recess portion which fits in or on the recess portion or the protruding portion formed on the rear end face.

BRIEF DESCRIPTION OF THE DRAWINGS

FIGS. 12A and 12B are drawings illustrating another embodiment of a terminal surrounding member, in which FIG. 12A is a front end view of a rear side surrounding member and FIG. 12B is a rear end view of a front side surrounding member;

FIGS. 13A and 13B are drawings illustrating a further embodiment of a terminal surrounding member, in which FIG. 13A is a front end view of a rear side surrounding member and FIG. 13B is a rear end view of a front side surrounding member;

FIGS. 14A and 14B are drawings illustrating an embodiment of a terminal surrounding member (an embodiment in which one recess portion and one protruding portion are provided), in which FIG. 14A is a front end view of a rear side surrounding member and FIG. 14B is a rear end view of a front side surrounding member;

DETAILED DESCRIPTION OF THE PREFERRED EMBODIMENTS

Figure 1:
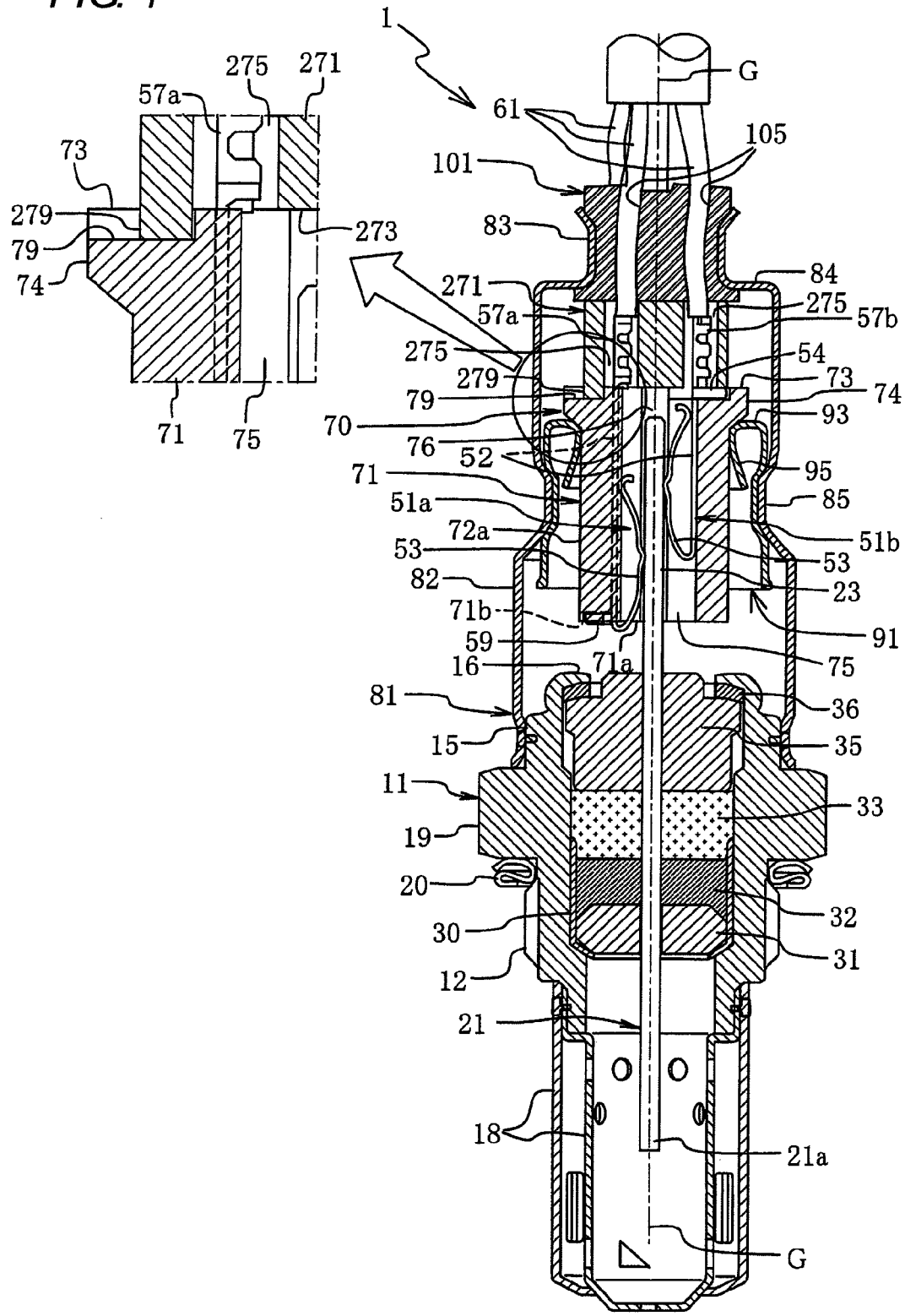
FIG. 1 is a front vertical sectional view showing an embodiment of a sensor of the invention and an enlarged view of a main part thereof.

A sensor 1 of the embodiment will be described in detail by reference to FIGS. 1 to 10. However, the present invention should not be construed as being limited thereto. Although a main part of the embodiment includes a feature in which a terminal surrounding member in the sensor is divided in a front-rear direction into two parts and in which a fitting structure like the one previously described is adopted, the sensor 1 will be described including an overall configuration thereof based on FIG. 1 showing the whole of the sensor 1 and other individual drawings which illustrate a terminal surrounding member. In the sensor 1 of the embodiment, the sensor element 21 is formed mainly from a ceramic into a long strip-like shape having a rectangular cross section and includes a detecting portion (not shown) 21a on a front end side (a lower end side in the figures). The sensor element 21 is disposed inside a cylindrical metal shell 11 (hereinafter, also referred to as a main body 11) and is fixed in place therein in an airtight condition. The metal shell 11 is formed into a concentrically stepped cylindrical shape in which its inner circumferential surface increases in diameter sequentially from a front end (a lower end in FIG. 1) towards a rear end thereof, and fixing threads 12 for mounting to an exhaust pipe (not shown) are formed on an outer circumferential surface at a portion close to the lower end.

An airtightness holding and fixing means for fixing the element 21 while maintaining airtightness is provided on an outer side of the element 21 inside the main body 11 so as to be filled therebetween. This airtightness holding and fixing means is made up of a holder 31 made of alumina and sealing materials (talc in this embodiment) 32, 33 disposed sequentially in that order from the bottom on an inner collar supported inside a tubular member 30 which is interposed at a lower step portion inside the main body 11. A sleeve 35 is disposed on the seal material 33. By inwardly bending a thin crimping cylindrical portion 16 (which is provided so as to extend continuously from a cylindrical portion 15 positioned at a portion of the main body 11 which lies near the rear end thereof) and compressing a rear end of the sleeve 35 towards a front end side of the main body 11 via a ring washer 36 so as to compress the inner sealing materials 32, 33, the element 21 is fixed inside the metal shell 11 in an airtight fashion.

The front end side of element 21 in which the detecting portion 21a is provided protrudes a predetermined amount (length) from a front end face of the main body 11, while a portion of the element 21 which is positioned near a rear end (an upper end in FIG. 1) thereof or a rear portion 23 of the element 21 protrudes a predetermined amount (length) from the rear end of the main body 11 and a rear end face of the sleeve 35. A protector (a protective cover) 18 provided with a plurality of holes (vent holes) and having a double-layer construction is placed on a front end (the detecting portion 21a) of the element 21 so as to surround the periphery thereof, and the protector 18 is fitted on the front end of the main body 11 and is fixed thereto. A large diameter portion 19 is formed on an outer circumference of the main body 11 at an intermediate portion in the direction of the axis G thereof so as to protrude therefrom, and this large diameter portion 19 constitutes a polygonal portion (a tool engagement portion) which is used to screw the main body 11 into an exhaust pipe (not shown). Also, a sealing gasket 20 is attached to a lower surface thereof.

A plurality of (for example, three) electrode terminals (metallized layers) 25 are formed side by side, as shown on a right side of FIG. 1, on each of side surfaces 24, 24 of the rear portion 23 of the element 21 closer to the rear end side. The element 21 is disposed and fixed within the main body 11 as described above, and protrudes from a rear end (an upper end in the figure) of the sleeve 35 (see a right side drawing in FIG. 1). In this embodiment, however, an electrode terminal 25 which is positioned centrally between electrode terminals 25 which are positioned on both lateral edges of the side surface 24, is positioned further rearward (upwards in the figure) than those on the lateral edges. In this manner, the central electrode terminal 25 and the electrode terminals 25 on the lateral edges are formed in positions which are not superposed one on top of the other in the front-rear direction (in a vertical direction in the figure). The electrode terminals 25 are provided for picking up a detected output from the detecting portion 21a and for applying a voltage to a heater, not shown, which is formed on the element 21. The electrode terminals 25 are formed by calcining together with the element 21.

Figure 17:
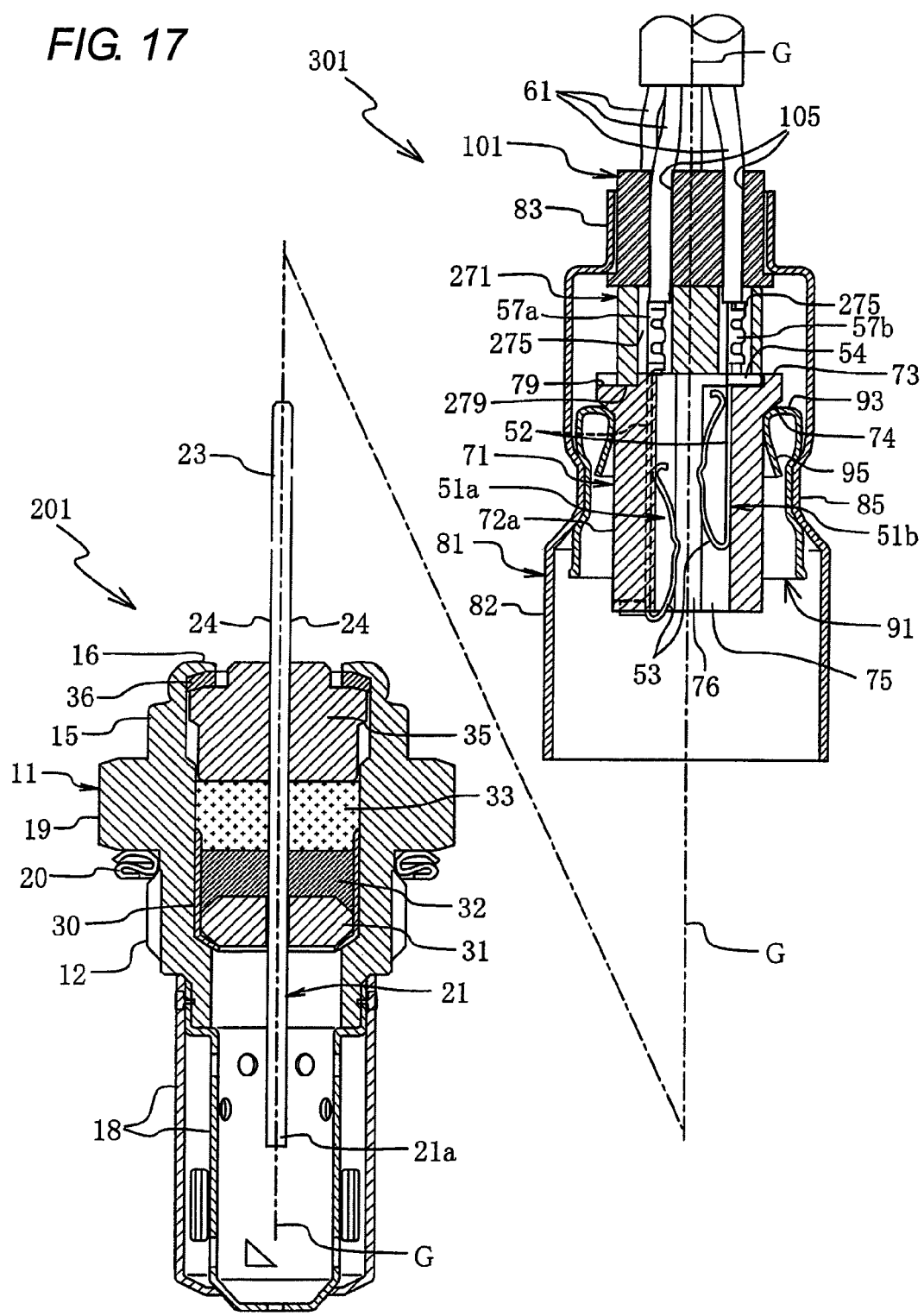
FIG. 17 is a drawing illustrating a step of fabricating the sensor of FIG. 1.
Figure 18:
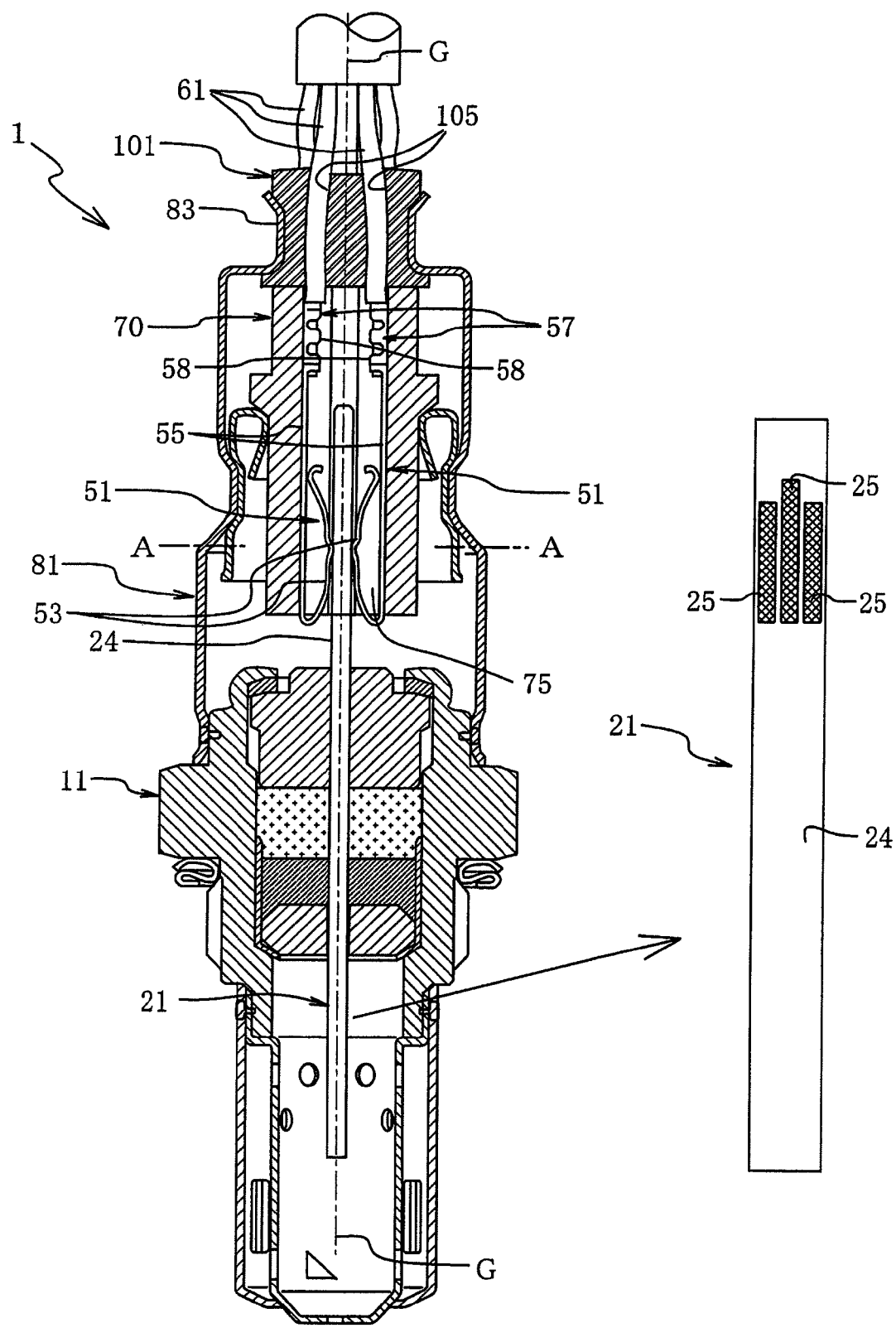
FIG. 18 shows a front vertical sectional view illustrating a conventional sensor and a side view of a sensor element.
Figure 19:
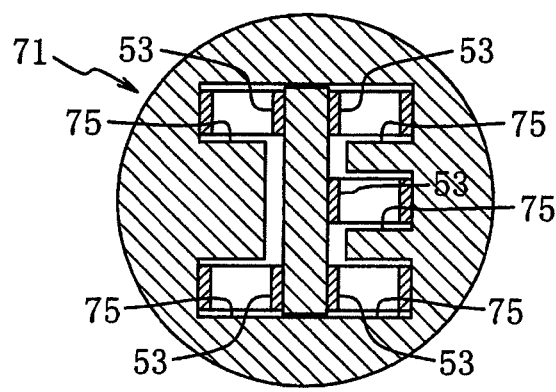
FIG. 19 is a cross-sectional view of a terminal surrounding member taken along the line A-A in FIG. 18.
Figure 20:
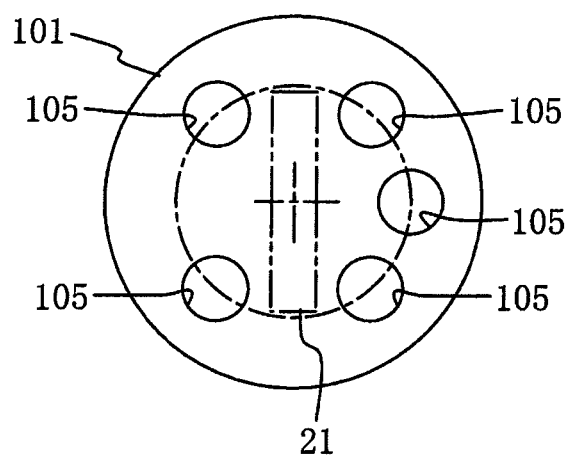
FIG. 20 is a drawing showing an arrangement of through holes that are to be provided in a sealing elastic element for insertion of lead wires.

Thus, what has been described heretofore is a substantially front end side half part (a substantially lower half part of FIG. 1) of the sensor 1 of the embodiment, and corresponds to an element side assembly half 201, shown in a bottom left part of FIG. 17, in which the element 21 is fixed within the main body 11. The sensor 1 of the embodiment is fabricated by assembling together the element side assembly half 201 and a terminal metal fitting side assembly half 301 including a terminal surrounding member 70 as a main part of the embodiment, shown in a top right part of FIG. 17, which constitutes a substantially rear end side half part (a substantially upper half part of FIG. 1) of the sensor 1 as described below. Next, The substantially rear end side half part of the sensor 1 which constitutes the terminal metal fitting side assembly half 301 including the terminal surrounding member 70 will be described in detail.

Namely, a cylindrical protective sleeve 81 having different diameters is disposed on a rear end side of the sensor 1, and the terminal surrounding member 70, which is made of an insulating material (a ceramic) and which has a circularly tubular or cylindrical shape, is disposed such that the axis line of the surrounding member 70 is coaxial with an axis line G of the metal shell 11 at the rear portion 23 of the element 21 inside the protective sleeve 81. Next, the terminal surrounding member 70 will be described in detail with reference to FIGS. 2 to 10. Although described in detail below, the terminal metal fittings 51b and terminal metal fittings 51a are disposed within the terminal surrounding member 70 and are electrically connected to the electrode terminals 25 on the respective side surfaces 24 of the element 21 by pressing their terminal connecting portions 53 serving as terminal connecting portions against the corresponding electrode terminals 25.

Figure 2:
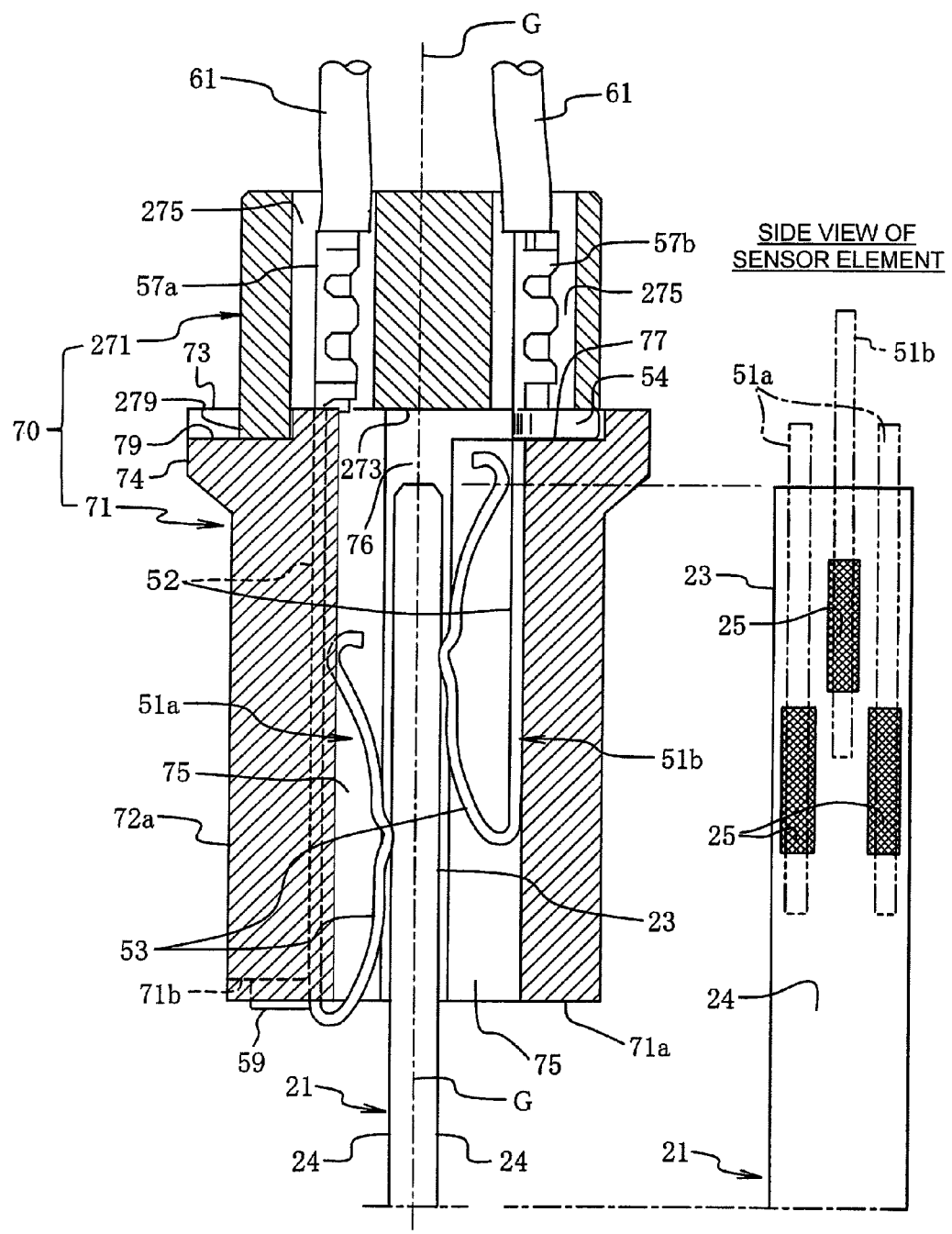
FIG. 2 is an enlarged view of the main part of FIG. 1 which includes a terminal surrounding member, and a right or left side view of a sensor element in the same figure.
Figure 3:
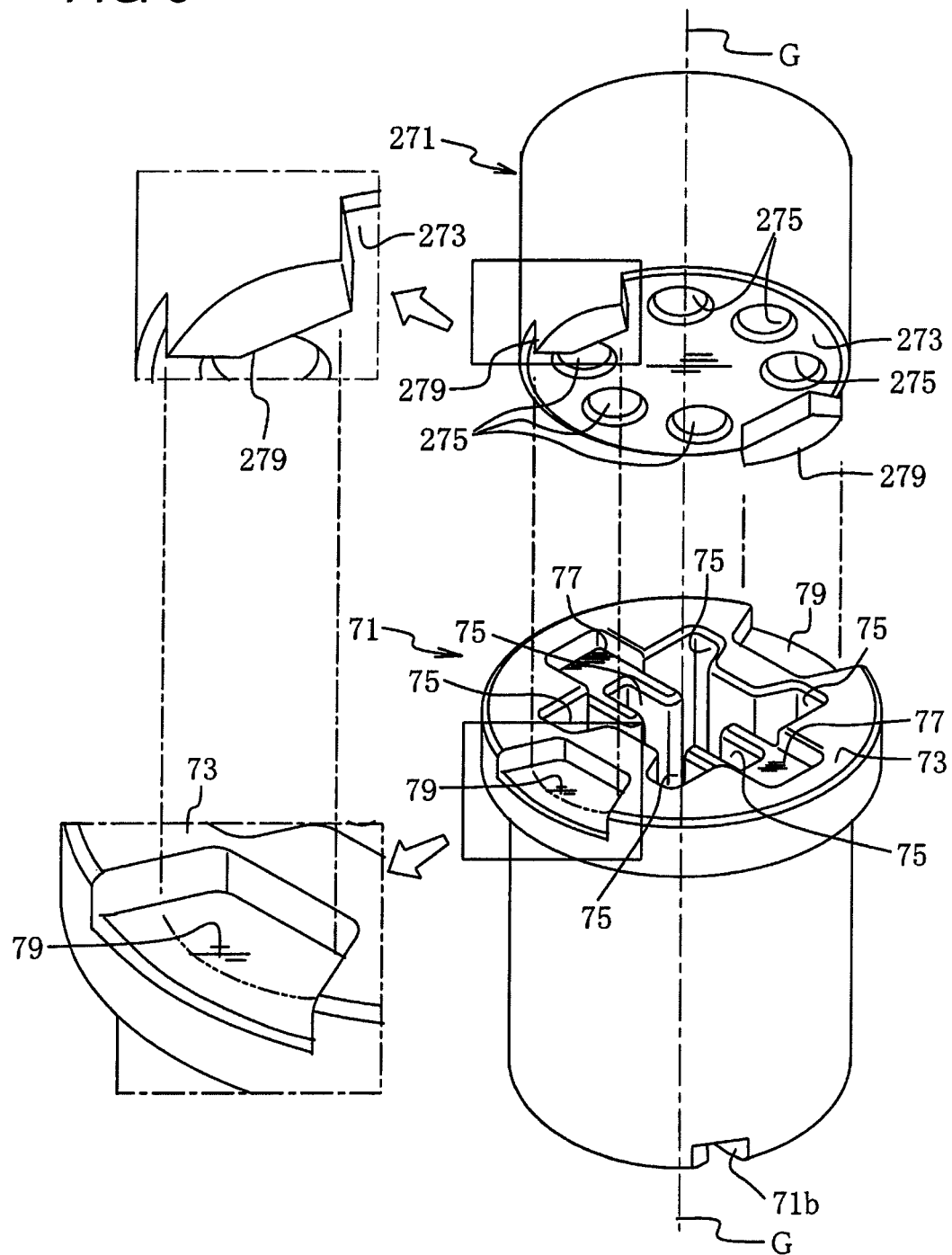
FIG. 3 is a drawing illustrating a front side surrounding member and a rear side surrounding member used in the sensor of FIG. 1, a lower part being a perspective view of the front side surrounding member when viewed from a rear end side thereof, and an upper part being a perspective view of the rear side surrounding member when viewed from a front end side thereof.

As shown in FIG. 2 and other figures, the terminal surrounding member 70, which is disposed concentrically within the protective sleeve 81 is divided in a front-rear direction into a front side surrounding member 71 which is positioned on a front end side, and a rear side surrounding member 271 which is positioned on a rear end side of the terminal surrounding member 70. These surrounding members 71, 271 both have a circularly tubular or cylindrical shape, and a rear end face 73 of the front side surrounding member 71 and a front end face 273 of the rear side surrounding member 271 abut each other.

Figure 4:
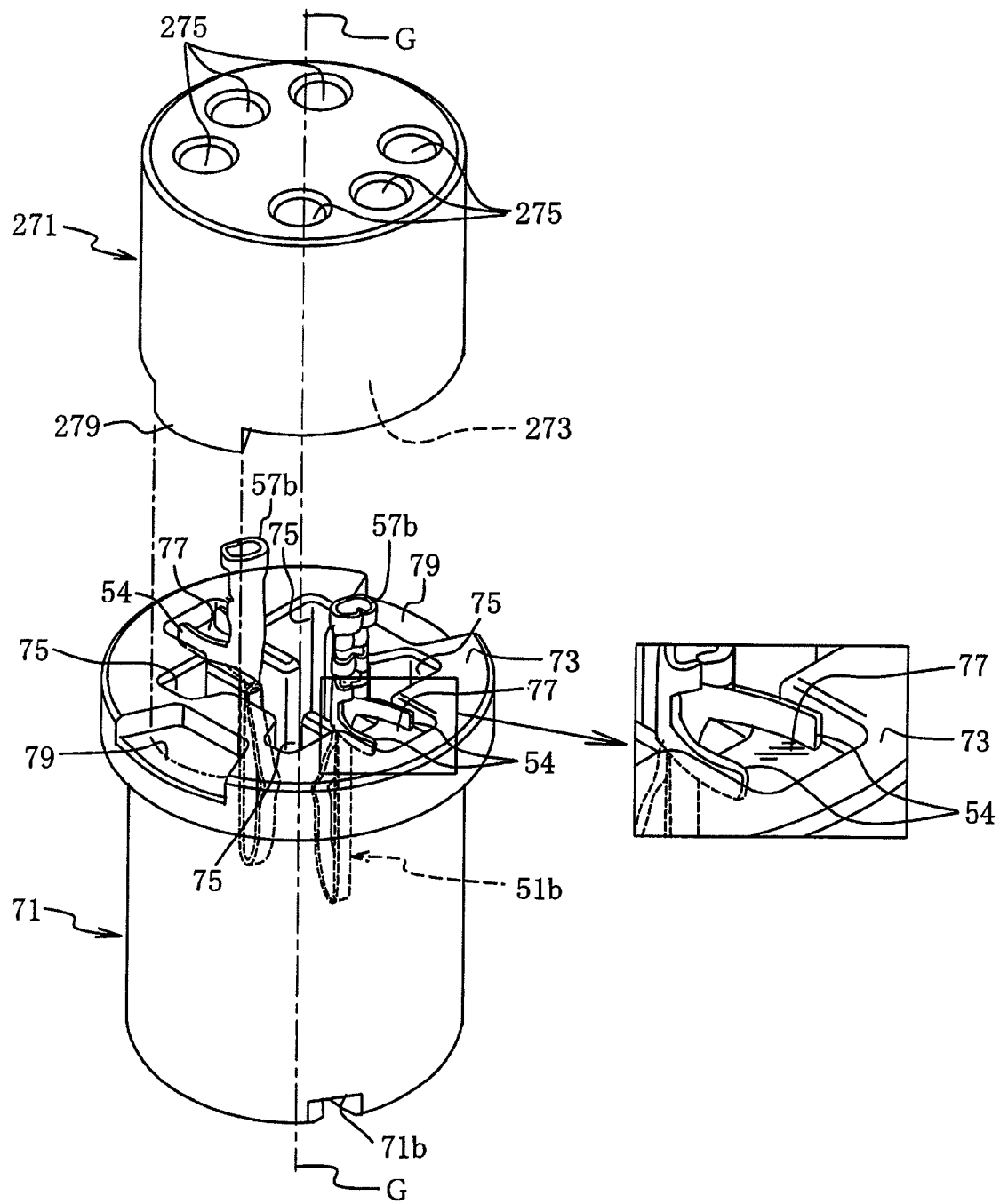
FIG. 4 is an exploded view illustrating the front side surrounding member and the rear side surrounding member used in the sensor of FIG. 1 when viewed from a rear end side of the sensor.
Figure 5:
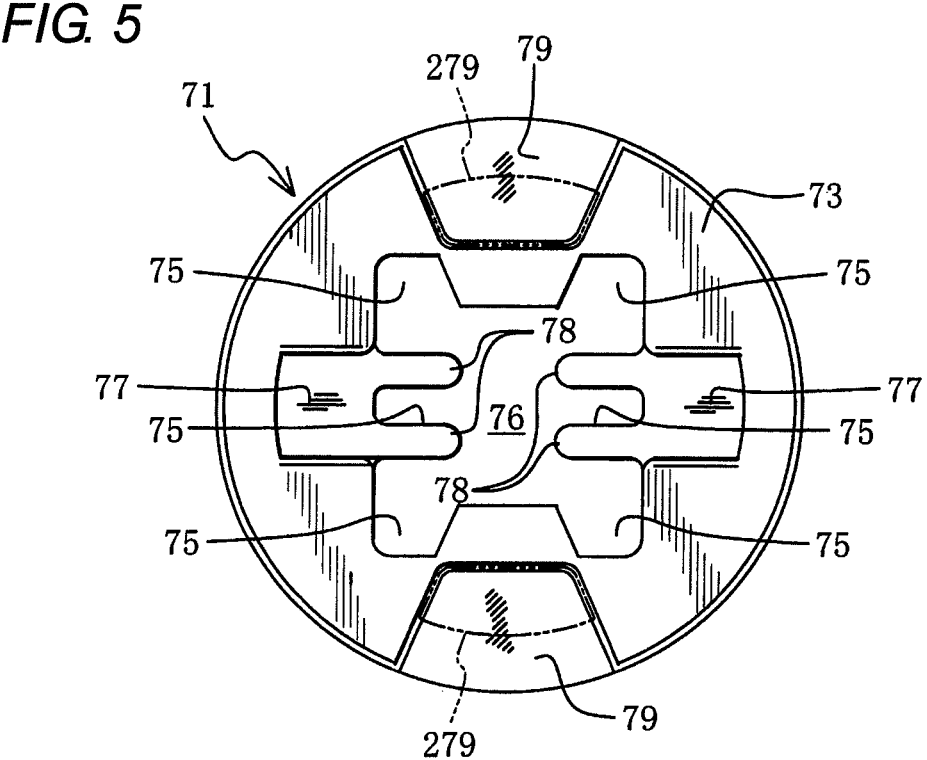
FIG. 5 is a rear end view of the front side surrounding member used in the sensor of FIG. 1.
Figure 6:
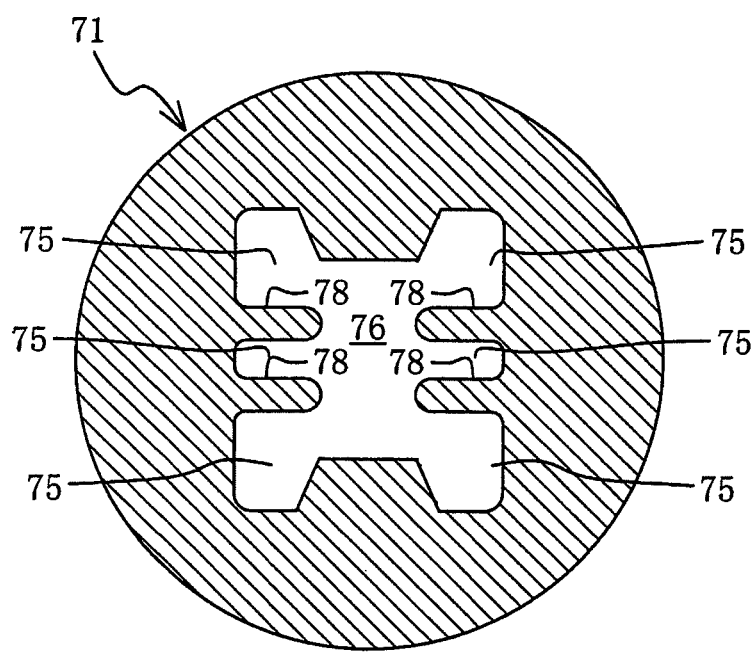
FIG. 6 is a cross-sectional view of the front side surrounding member illustrating holes in the front side surrounding member of FIG. 5.
Figure 7:
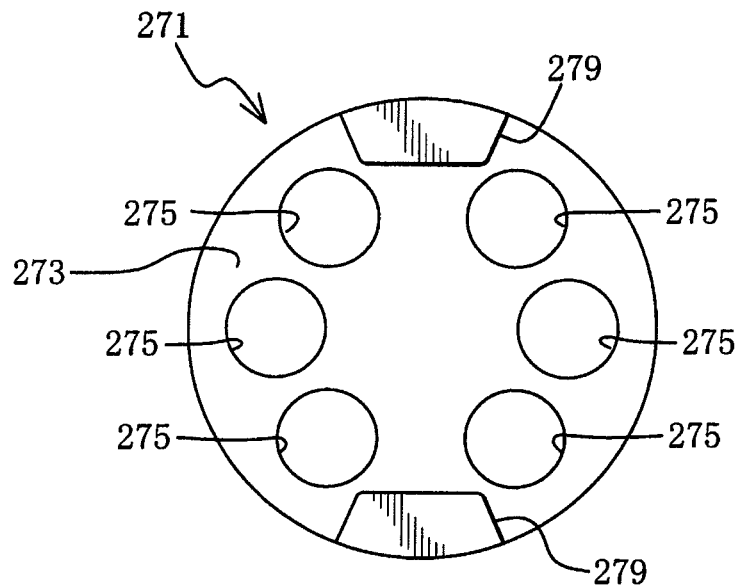
FIG. 7 is a front end view of the rear side surrounding member used in the sensor of FIG. 1.
Figure 8:
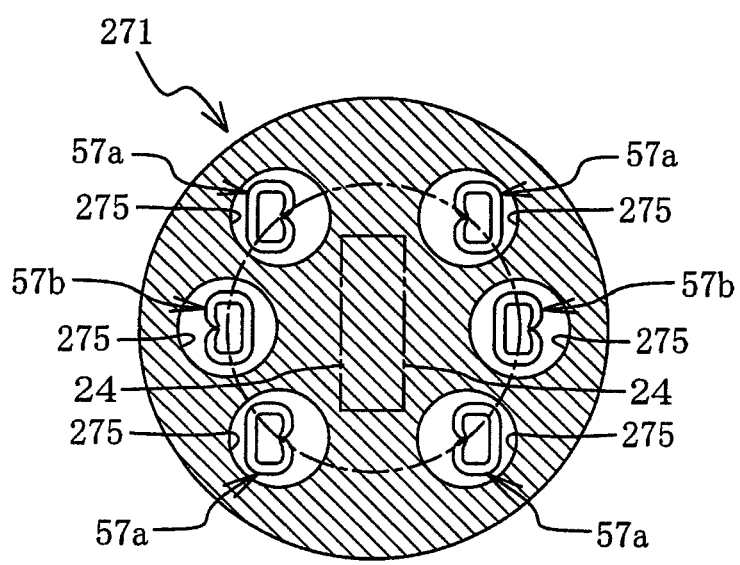
FIG. 8 is a cross-sectional view of the rear side surrounding member illustrating holes therein with terminal metal fittings disposed in the holes.
Figure 9:
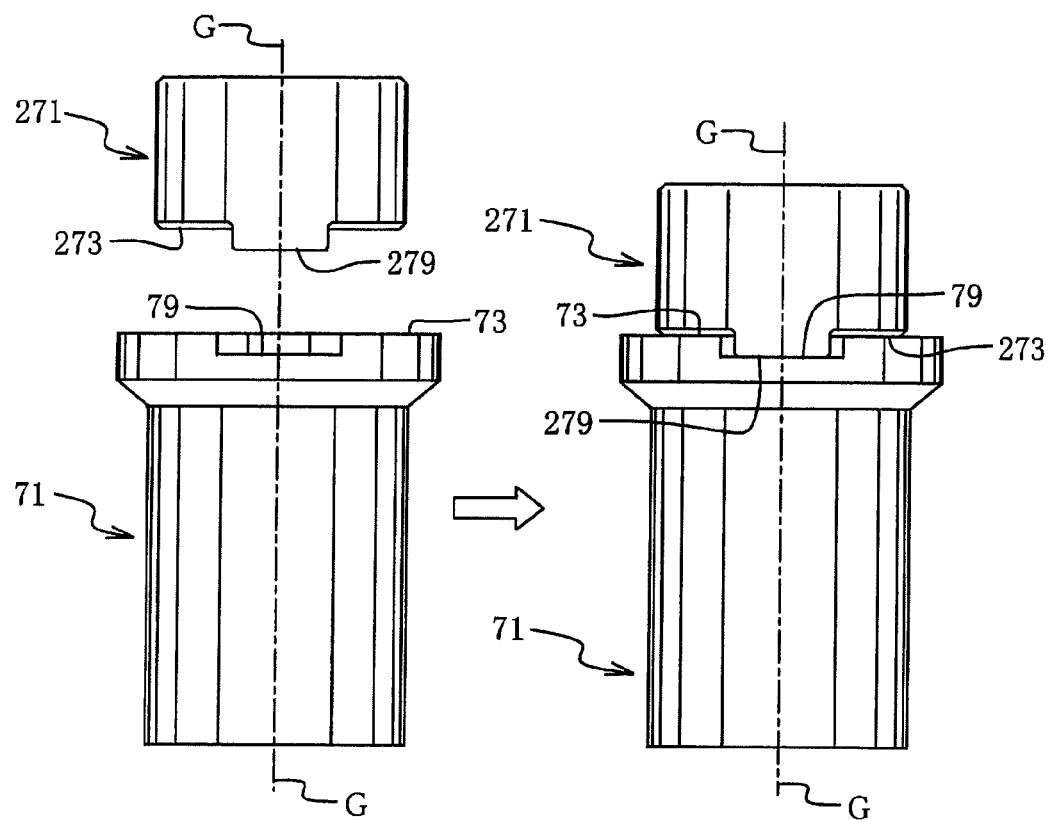
FIG. 9 is a drawing illustrating a step of abutting the front side surrounding member and the rear side surrounding member to each other by fitting a protruding portion on a front end face of the rear side surrounding member in a recess portion on a rear end face of the front side surrounding member.
Figure 10:
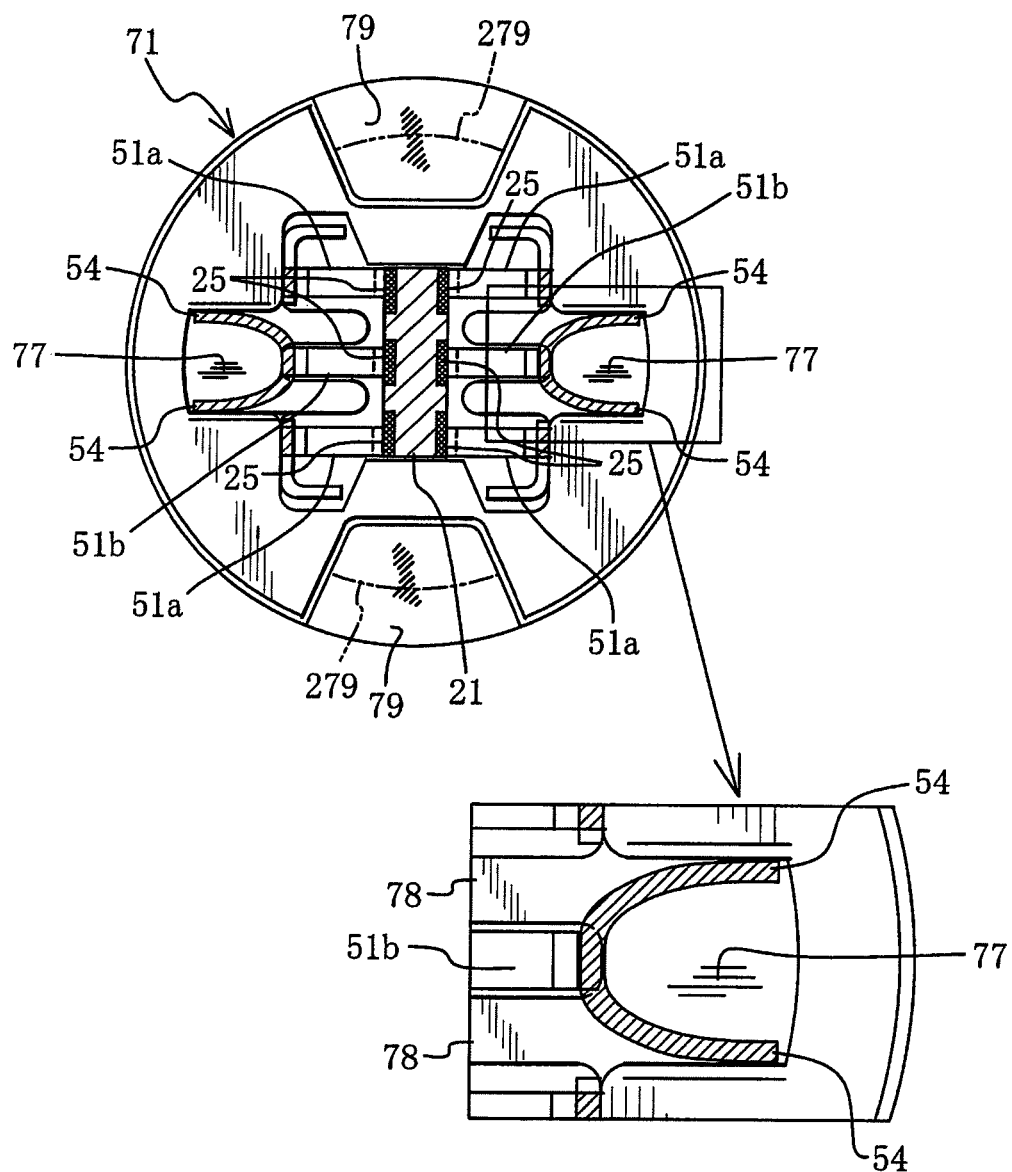
FIG. 10 is a rear end view of the front side surrounding member in which an element and the terminal metal fittings are disposed.

Of these end faces, two recess portions 79 are formed on the rear end face 73 of the front side surrounding member 71 so as to be recessed towards a front end side of the terminal surrounding member 70. The recess portions 79 are formed into being exposed on a portion of an outer circumferential surface of the front side surrounding member 71, and the two recess portions 79 are disposed in symmetrical positions across an axis G of the front side surrounding member 71 (see FIGS. 2 to 5). These recess portions 79 have a trapezoidal shape (a fan-like shape) in which a side facing the center (axis G) of the front side surrounding member 71 is narrowed as shown in FIG. 5 in plan view or when viewed from a rear end side of the front side surrounding member 71. The front side surrounding member 71 has therein a hollow portion 76 into which the element 21 can be inserted at a center of the front side surrounding member 71 and three terminal metal fitting inserting holes 75 on each side thereof. The holes 75 are arranged so as to surround the hole portion 76 (see FIGS. 5 and 6). As shown in FIGS. 5, 6 and 10, the terminal metal fitting holes 75 on each side are partitioned by walls (bulk heads) 78 (see FIG. 6 and the like) which extend in the front-rear direction so as to ensure electrical insulation between the terminal metal fittings 51a, 51b which are disposed adjacent to each other. In this embodiment, another caved-in (recess) portion 77 is formed at an opening of a center hole 75 on each side on the rear end face 73 so as to extend outwardly of the center hole 75 in addition to the recess portion 79. Although described in detail below, the caved-in portion 77 is formed so that a protruding piece portion 54 which is provided on the centrally disposed terminal metal fitting 51b fits therein. In this embodiment, a flange portion 74 is provided on an outer circumference of a rear end portion of the front side surrounding member 71 so as to protrude therefrom.

On the other hand, protruding portions 279 are provided on the front end face of the rear side surrounding member 271 so as to protrude to a predetermined height towards a front end side of the terminal surrounding member 70, and these protruding portions 279 are adapted to fit in the two recess portions 79 individually. Holes 275 having a circular cross section are provided in an interior of the rear side surrounding member 271 in an arrangement which corresponds to the arrangement of the holes 75 in the front side surrounding member 71. In this manner, the clamping portions of the terminal metal fittings (which are disposed in the corresponding holes 75 in the front side surrounding member 71) can be disposed in the holes 275 in a state such that both of the surrounding members abut the protruding portions 279 fitted in the recess portions 79. In the embodiment, however, the holes 275 (in which clamping portions 57b of the terminal metal fittings 51b which are connected to the center electrode terminals 25 of the respective side surfaces 24 of the element 21 are disposed) are provided so as to be offset further outwards of an axis G of the rear side surrounding member 271 than the holes 75 in the front side surrounding member 71.

The terminal surrounding member 70 of the sensor 1 of the embodiment is made by abutting the rear end face 73 of the front side surrounding member 71 and the front end face 273 of the rear side surrounding member 271, and has a fitting structure in which the protruding portions 279 provided on the front end face 273 fit in the recess portions 79 provided on the rear end face 73. The axes G of the front side surrounding member 71 and the rear side surrounding member 271 are set to coincide when the protruding portions 279 fit in the recess portions 79. This configuration prevents either of the front side surrounding member 71 and the rear side surrounding member 271 from rotating about its own axis G relative to the other within the sensor 1. In addition, this configuration also prevents the front side surrounding member 71 and the rear side surrounding member 271 from deviating in the lateral direction so that the axes G of both the surrounding members are offset.

In the sensor 1 of this embodiment, the rear portion of the element 21 is inserted in the center hole 76 in the front side surrounding member 71, and the terminal metal fittings 51a, 51b are disposed in the holes 75, 275 in the interiors of both the surrounding members 71, 271. Terminal connecting portions 53 of the terminal metal fittings 51a, 51b are pressed against the electrode terminals 25 on the element 21 by making use of their spring characteristics for ensuring electrical connections therebetween. Namely, in this embodiment, the three terminal metal fittings are disposed on each of opposing sides and in the terminal surrounding member 70 so as to face respective side surfaces 24 (left and right side surfaces in FIGS. 1 and 2) of the element 21 while holding the element 21 therebetween (see FIG. 10). The terminal connecting portions 53 are pressed against the corresponding electrode terminals 25 by making use of their spring characteristics.

In this embodiment, the protruding piece portion 54 is provided on the terminal metal fitting 51b which is shown on a right side in FIGS. 1 and 2. The protruding piece portion 54 is designed to be held between the rear end face 73 of the front side surrounding member 71 and the front end face of the rear side surrounding member 271. As described above, however, the caved-in portions 77 are formed separately from the recess portions 79 on the rear end face 73 of the front side surrounding member 71. As shown in FIGS. 2, 4 and 10, the protruding piece portions 54 of the terminal metal fittings 51b are fitted in the caved-in portions 77. This configuration restricts the terminal metal fittings 51b from rotating about imaginary axes (not shown) which extend in the front-rear direction within the terminal holes 75, and also prevents the terminal metal fitting 51b from moving along the front-rear direction relative to the terminal surrounding member 70.

Figure 11:
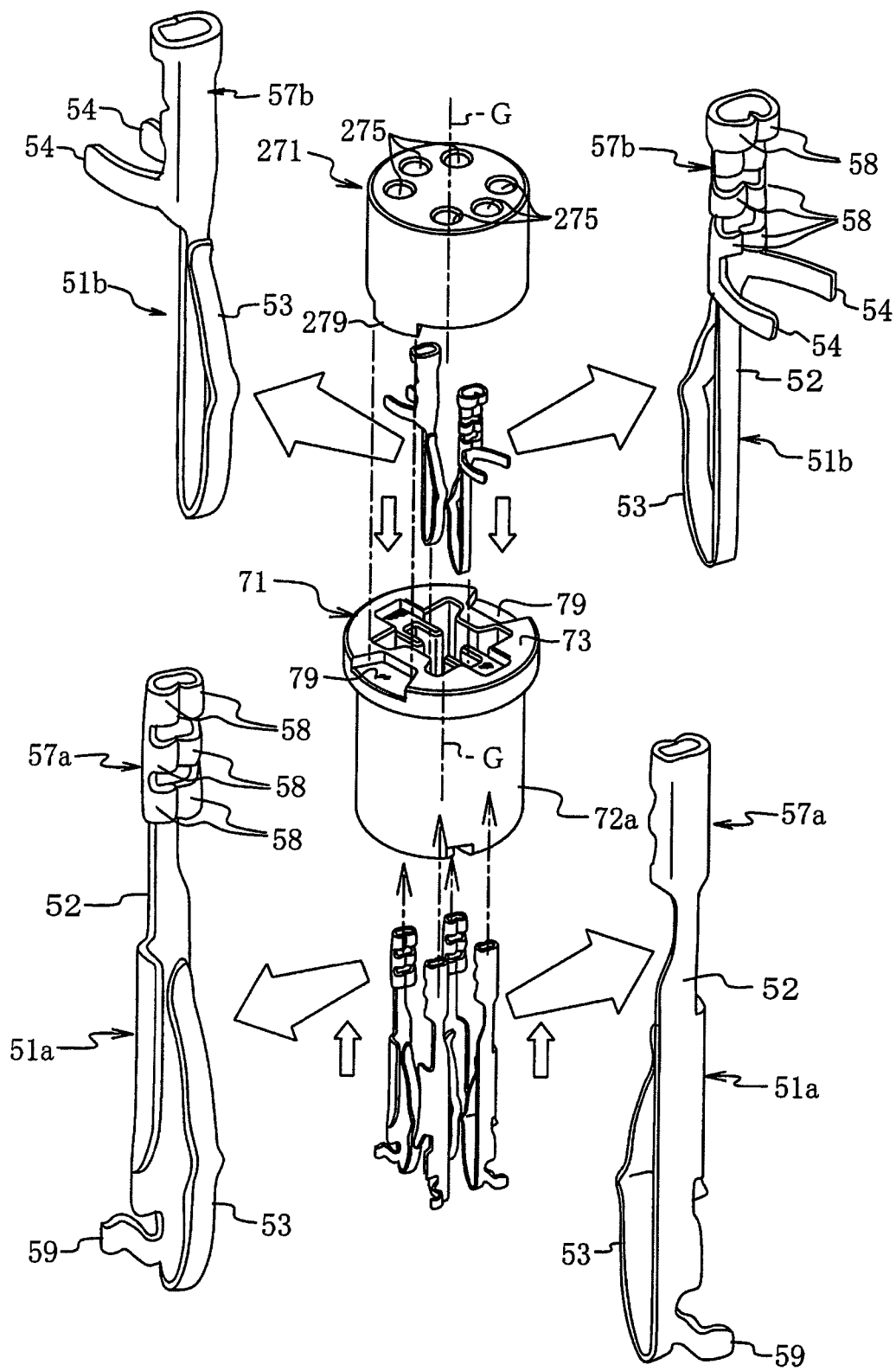
FIG. 11 is an exploded perspective view illustrating the terminal surrounding member and the terminal metal fittings which make up the sensor of FIG. 1.

The terminal metal fittings 51a, 51b are bent and folded back at front ends of terminal metal fitting main bodies (relay wire portions) 52 which extend in the front-rear direction into an arc-like shape which protrude convexly on a side facing the element 21 (a side facing the axis G in FIGS. 1 and 2), so as to form the terminal connecting portions 53 having spring characteristics. By pressing the terminal connecting portions 53 against the corresponding electrode terminals 25 on the respective side surfaces 24 of the element 21, and by making use of their spring characteristics within the individual holes 75, electrical connection therebetween is ensured. In this embodiment, with regard to the terminal metal fittings 51a, 51b which are disposed in the terminal holes 75 formed on one of the sides of the terminal surrounding member 70 which hold the element 21 therebetween, the terminal metal fittings 51a disposed in the terminal holes 75 positioned on outer sides (lateral edge sides) in a width direction of the element 21 are different from the terminal metal fitting 51b disposed in the center terminal hole 75 as described above (see FIG. 11). In FIGS. 1 and 2, the terminal metal fitting 51a positioned on a left side of the axis G is shown as one of the terminal metal fittings 51a which are positioned on the outer sides, and the terminal metal fitting 51 positioned on a right side of the axis G is shown as the center terminal metal fitting 51b. The center terminal metal fitting 51b is formed shorter than the other terminal metal fittings.

On each side surface 24 of the element 21, crimping pieces 58 which constitute clamping portions 57a of the terminal metal fittings 51a, 51a which are positioned on the lateral edge sides are bent towards the element 21 (towards the electrode terminal) so as to clamp lead wires 61 (front ends of core wires) for connection. On the other hand, a crimping piece 58 which constitutes the clamping portion 57b of the centrally positioned terminal metal fitting 57b is bent towards an opposite side to the electrode terminal 25 so as to clamp a lead wire 61 for connection (see FIGS. 1, 2 and 11). Each of the terminal metal fittings 51a, 51a positioned at the lateral edge sides includes, at the front end thereof, a hook (lance) 59 which protrudes so as to be locked in a groove-like recess portion 71b at a front end face 71a of the front side surrounding member 71 to thereby prevent movement thereof in the rear direction (see FIG. 11).

In the sensor 1 of the embodiment, the individual lead wires 61 are passed through the through holes 105 which are formed so as to extend through the sealing elastic member 101 which is compressed diametrically at the rear end of the protective sleeve 81, and are then led out of the rear end (upper end in the figure) of the metallic protective sleeve 81. The through holes 105 are formed substantially in the same arrangement as that of the terminal holes 275 of the rear side surrounding member 271.

As shown in FIG. 1, the protective sleeve 81, which is formed into the cylindrical shape having different diameters, is disposed on the circumferences of the front side surrounding member 71 and the rear side surrounding member 271 which make up the terminal surrounding member 70 so as to surround both of the surrounding members. The protective sleeve 81 has at its rear end a sealing sleeve portion 83 which is formed into a concentric cylindrical shape so as to have a relatively small diameter via an annular shoulder portion 84 which extends continuously therefrom towards the axis G, and the sealing elastic member 101 is disposed within the sealing sleeve portion 83. The protective sleeve 81 has at its front end (a lower end in the figure) side a large diameter sleeve portion 82 which has a larger diameter than that of the sealing sleeve portion 83. The sealing sleeve portion 83 fits on a cylindrical portion 15 of the metal shell 11 which is provided at a rear portion thereof at the large diameter sleeve portion 82, and an outer circumferential surface of the fitting portion is crimped, for example, and is thereafter fixed to the main body 11 by welding.

In this embodiment, as shown in FIG. 1, a cylindrical supporting member 91 whose rear end 93 is bent inwards in a fold-back fashion when viewed in a vertical section is disposed concentrically within an annular space defined between an inner circumferential surface of the large diameter sleeve portion 82 of the protective sleeve 81 and the front side surrounding member 71, and is fixed to an inner surface of the protective sleeve 81. This supporting member 91 is made of a metallic plate (a thin plate) into a substantially cylindrical shape and has a spring piece 95 which is formed by being bent in a fold-back fashion at the rear end 93 thereof. An intermediate portion 85 of the large diameter sleeve portion 82 of the protective sleeve 81 is crimped to thereby become deformed and contract in diameter in the direction of the axis G. By such deformation, the spring piece 95 is pressed against an outer circumferential surface 72a of the front side surrounding member 71, whereby the front side surrounding member 71 is fixed in place within the protective sleeve 81. In this embodiment, the fold-back portion at the rear end (the upper end) 93 of the supporting member 91 is disposed so as to be locked on a surface of the flange 74 of the front side surrounding member 71 which is oriented towards the front end, and a rear end of the rear side surrounding member 271 is disposed so as to be locked on a surface of the sealing elastic member 101 fixed within the protective sleeve 81 which is oriented towards the front end, whereby the terminal surrounding member 70 which is made by abutting the two surrounding members is prevented from moving in the front-rear direction within the sensor 1.

The following advantages can be obtained by the sensor 1 of the embodiment which is configured as described heretofore. Namely, in the terminal surrounding member 70 which makes up the sensor 1 of the embodiment, the front side surrounding member 71 and the rear side surrounding member 271 abut each other at their end faces 73, 273 and are also fitted together at the recess portions 79 and the protruding portions 279 in the manner described above. Because of this, in the fitting condition, both the surrounding members 71, 271 do not rotate relative to each other about the axis G, and moreover, both the surrounding members 71, 271 do not deviate laterally from each other, whereby both the surrounding members 71, 271 are disposed stably within the sensor 1. Consequently, the terminal metal fittings 51a, 51b which are disposed in the corresponding holes 75, 275 in both the surrounding members 71, 271 do not move and hence are not deformed, whereby reliable electrical connection with the electrode terminals 25 on the element 21 is maintained.

Moreover, since a two-part structure is adopted in which the terminal surrounding member 70 is divided in the front-rear direction into the two surrounding members, the degree of freedom in designing the structure of the holes 75, 275 formed therein and the shape and structure of the terminal metal fittings which are disposed within the holes 75, 275 is enhanced. Namely, since the two-part structure is adopted, when the terminal surrounding member 70 is regarded as a single terminal surrounding member, although the individual holes are not straight in the front-rear direction, the holes can be formed without any problem. Further, since a plurality of recess portions 79 and protruding portions 279 are formed on the rear end face 73 and the front end face 273, respectively, both of the members can be prevented from rotating relatively about their axes and from deviating laterally from each other without specifying the shapes of the recess portions 79 and the protruding portions 79.

In the embodiment, the protruding piece portions 54 are formed on the terminal metal fittings 51b in the manner described above, so that the protruding piece portions 54 are held between the end faces of both the surrounding members 71, 271, and this configuration can prevent the terminal surrounding member 70 from moving in both the rear and front directions. In addition, in this embodiment, the protruding piece portions 54 on the terminal metal fittings 51b not only are held simply between the end faces, but also fit in the cave-in portions 77 described above. Consequently, even when the rear ends of the terminal metal fittings 51b or the head wires 61 which are connected thereto are twisted about their axes (imaginary axes) which extend in the front-rear direction, the terminal metal fittings 51*b* do not rotate about the imaginary axes within the holes in the terminal surrounding member 70 in which the terminal metal fittings are disposed. In the embodiment, the recess portions 79 are formed on the rear end face 73 of the front side surrounding member 71 at positions lying closer to the outer circumference by cutting out portions of the outer circumferential surface. This configuration is preferable when the front side surrounding member is made of a ceramic because the recess portions 79 can be formed without affecting the arrangement of the holes 75 through which the terminal metal fittings are inserted, and because the structure of the recess portion 79 can be embodied as a simple structure in which no wall is provided on an outer circumferential surface side thereof.

In the embodiment, the two recess portions 79 are described as being formed on the rear end face 73 of the front side surrounding member 71 and the two protruding portions 279 are described as being formed on the front end face of the rear side surrounding member 273. In contrast, from a technical point of view, a configuration may be adopted in which the protruding portions are formed on the rear end face 73 of the front side surrounding member 71 and the recess portions are formed on the front end face 273 of the rear side surrounding member 271. Additionally, for example, a configuration may be adopted in which one recess portion and one protruding portion are provided on the rear end face 73 of the front side surrounding member 71, and one protruding portion and one recess portion are provided on the front end face 273 of the rear side surrounding member 271. Namely, the invention may have a fitting structure in which the recess portions and the protruding portions which are formed on either of the rear end face and the front end face fit on and in each other. Consequently, in a state in which the rear end face of the front side surrounding member, which is one of the two divided surrounding members, and the front end face of the rear side surrounding member, which is the other of the two divided surrounding members, abut each other, either of the two surrounding members is prevented from rotating about its own axis relative to the other and either of the two surrounding members is prevented from deviating relative to the other in a direction perpendicular to its own axis. As a result, the shapes of the end faces (the shapes resulting when viewed from the direction of the axis) of the recess portions and the protruding portions which make up the fitting structure and the numbers of recess portions and protruding portions can be embodied as required. Also, as to the number of recess portions and protruding portions, one or three or more recess portions and protruding portions may be provided at required portions on the respective end faces.

Figure 12A:
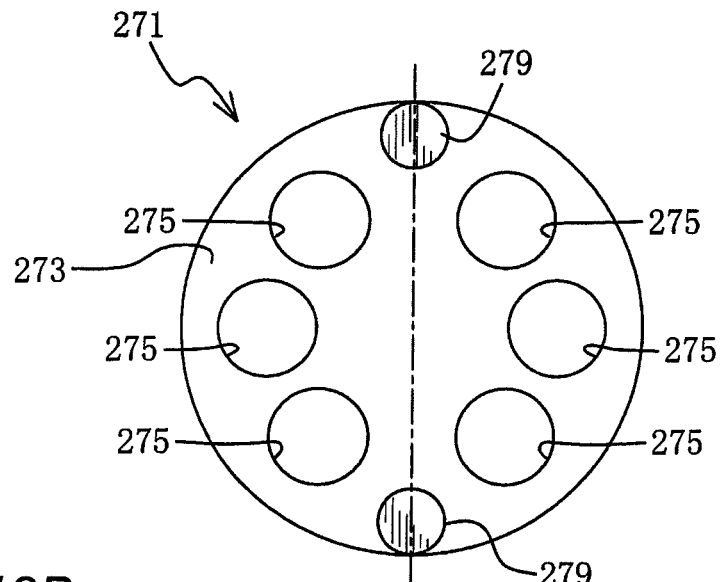
Figure 12B:
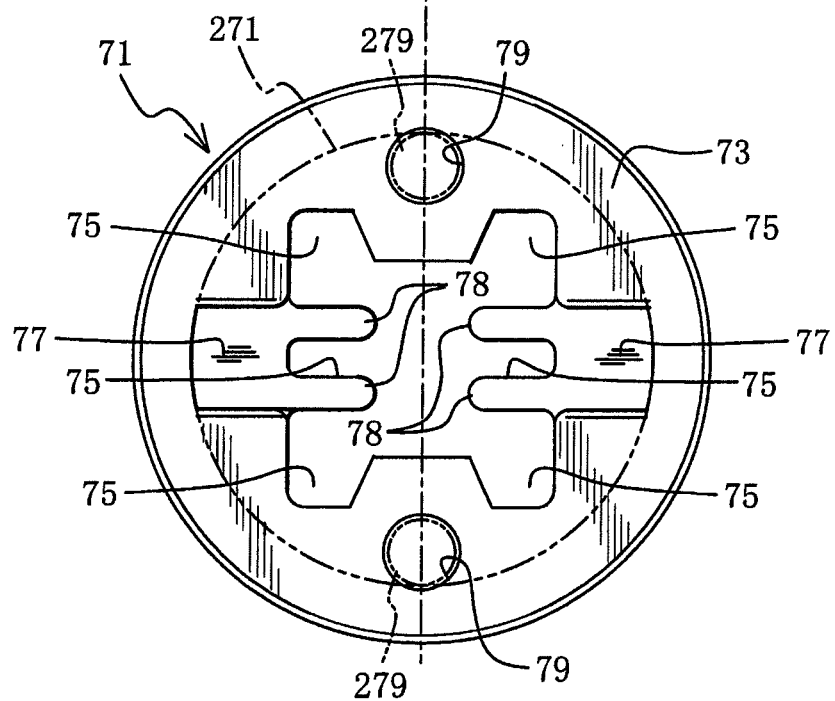
Figure 13A:
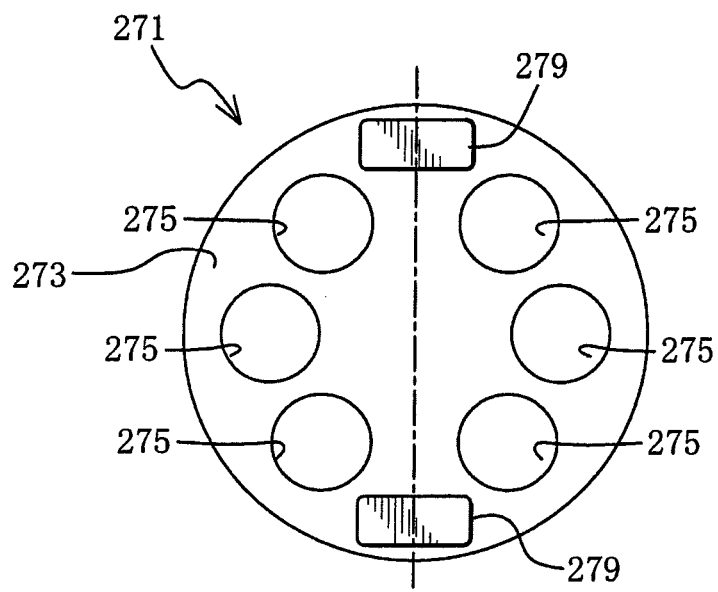
Figure 13B:
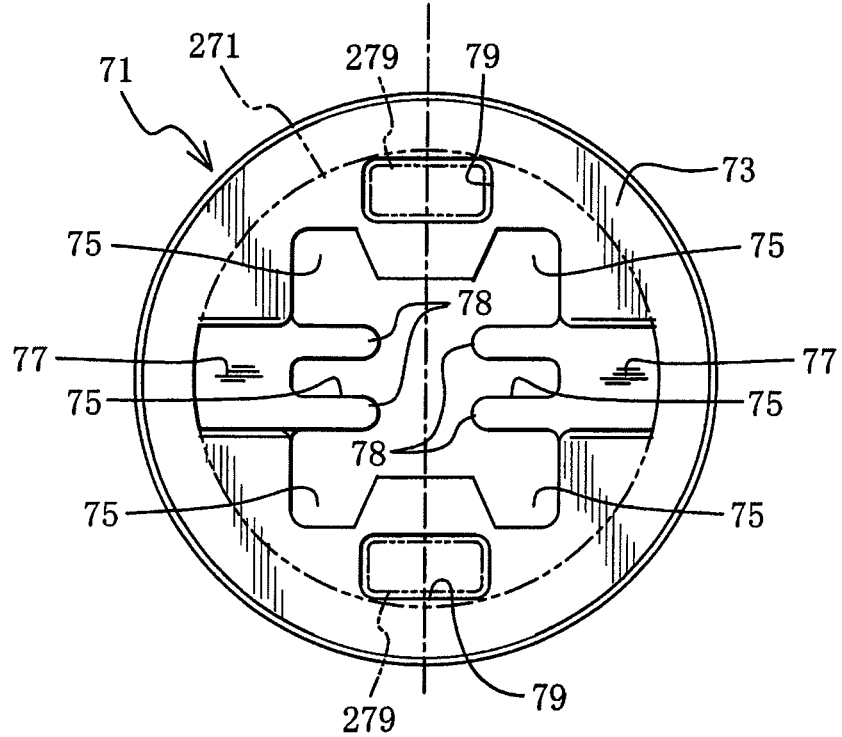

Specifically, the shape of the recess portion 79 which results when viewed from the rear end face 73 of the front side surrounding member 71 may be embodied into appropriate shapes including circular and rectangular shapes as shown in FIGS. 12B and 13B. FIGS. 12A and 13A show a rear side surrounding member 271 viewed from a front end face 273 thereof. Protruding portions 279 are formed on the front end face 273 in a rising fashion so as to fit into recess portions 79. In FIGS. 12 and 13, since constituent members other than the recess portions 79 and the protruding portions 279 are similar to those described in the embodiment above, like reference numerals are given to like members, and a description thereof will be omitted. This is also the case in the following example. As shown in FIG. 13B, the recess portions 79 which are formed on the rear end face 73 of the front side surrounding member 71 are formed into a rectangular shape when viewed from the rear end side thereof and are formed as independent holes, while the protruding portions 279 which are provided on the front end face 273 of the rear side surrounding member 271 are formed, as shown in FIG. 13A, so as to fit in the recess portions 79 which are made up of the rectangular holes with substantially no remaining gap. In this case, the number of recess portions 79 and protruding portions 279 can be reduced to one each.

Figure 14A:
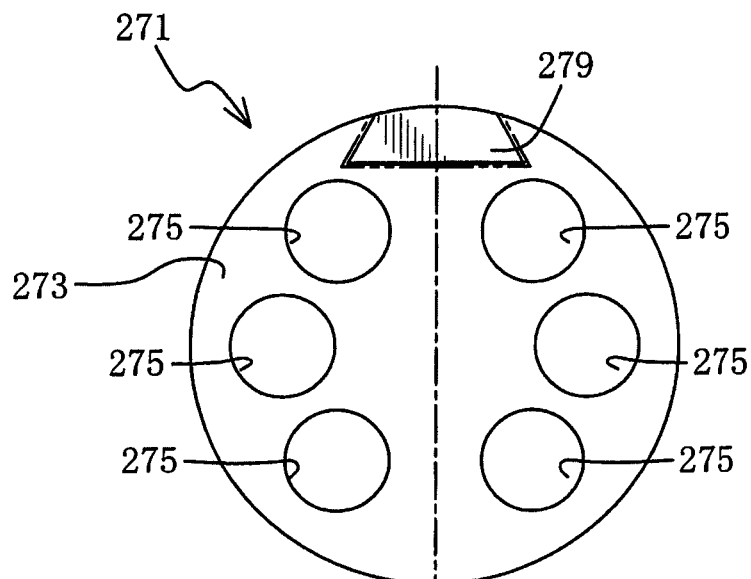
Figure 14B:
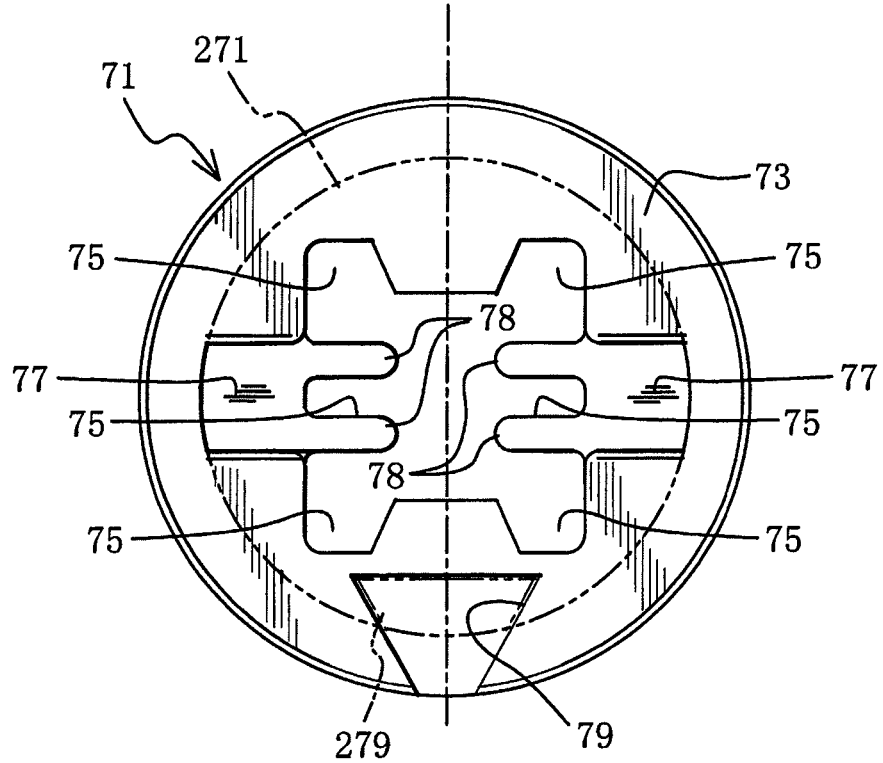

Further, assuming that the recess portions 79 are formed on the front side surrounding member 71, when the recess portions 79 are not exposed to the outer circumferential surface of the front side surrounding member 71, an elliptical shape or a polygonal shape can be selected. In a case where recess portions 79 are formed into being exposed on a portion of the outer circumferential surface of the front side surrounding member 71, as shown in FIG. 14, a trapezoidal shape in which an outer circumferential surface side portion becomes narrower than a center side portion of the front side surrounding member 71, an elliptical shape, a fan-like shape and the like can be selected.

Figure 15:
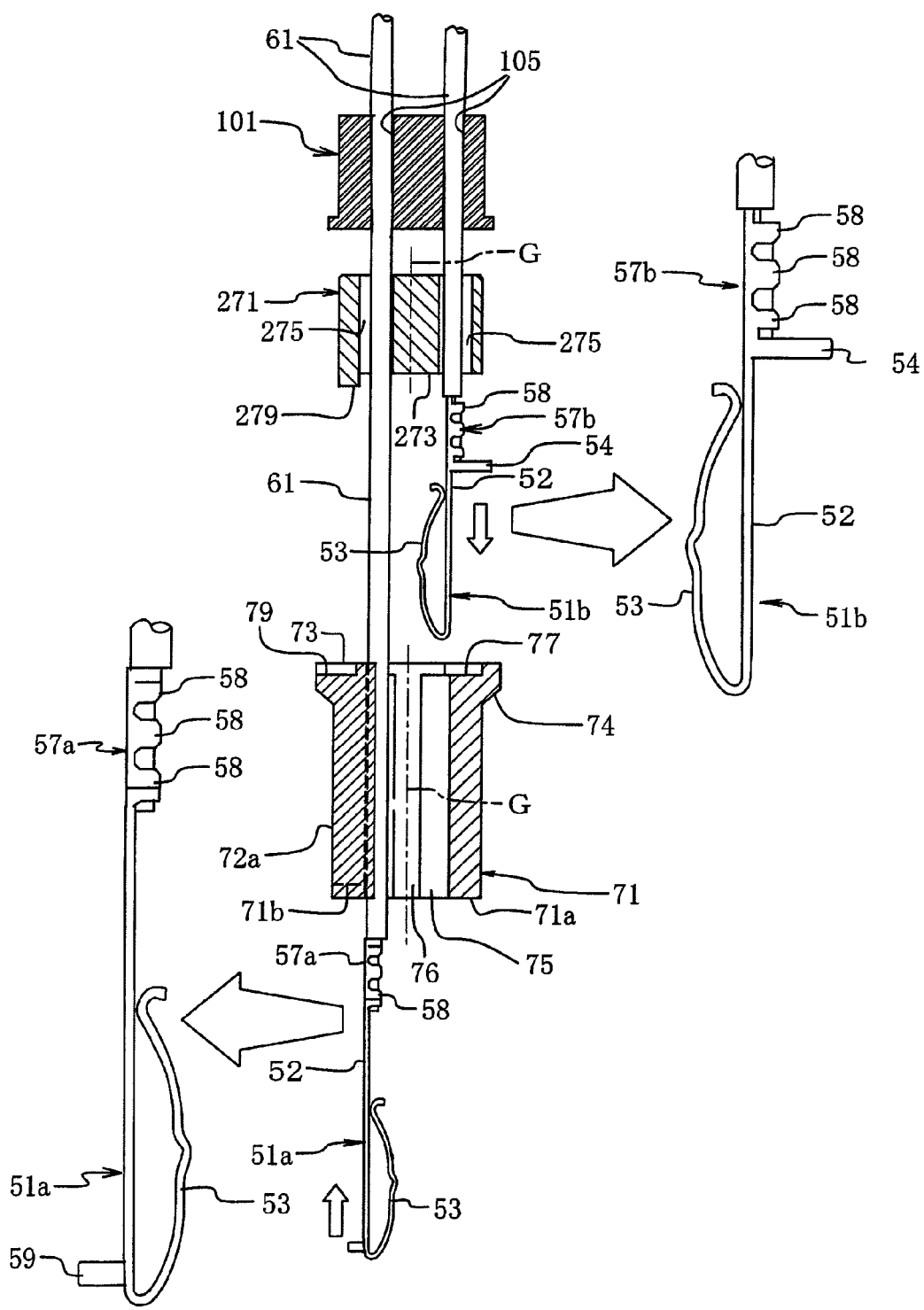
FIG. 15 is a drawing illustrating a step of fabricating the sensor of FIG. 1.

The sensor 1 in FIG. 1 can be fabricated by separately building the element side assembly half 201 shown at the left bottom part of FIG. 17 and the terminal metal fitting side assembly half 301 shown in the right top part of the same figure and combining them. Before describing the fabrication of the sensor 1, the building of the terminal metal fitting side assembly half 301 will be described in detail below (see FIGS. 15 and 16). Namely, end portions (front ends) of the individual lead wires 61 are passed through the through holes 105 provided in the sealing elastic member 101 and are also passed through the terminal holes 275 provided in the rear side surrounding member 271. As this occurs, the lead wires 61 other than the lead wires 61 connected to the central terminal metal fittings 51*b* are passed through the terminal holes 75 in the front side surrounding member 71 (see a left part of FIG. 15). Then, the crimping pieces 58 which constitute the clamping portions 57*a*, 57*b* at the rear ends of the terminal metal fittings 51*a*, 51*b* are bent and crimped in the manner described above so as to be connected to core wire portions at the end portions of the individual lead wires 61 (see FIG. 15). As this occurs, as shown in FIG. 15, any of the terminal connecting portions 53 is made to be oriented towards the corresponding side surface 24 of the element 21.

The respective terminal connecting portions 53 of the terminal metal fittings are inserted into the corresponding terminal holes 75 in the front side surrounding member 71 so as to be arranged in the manner described above, and the protruding piece portions 54 of the terminal metal fittings 51*b* are fitted in the cave-in portions 77 on the rear end face 73 of the front side surrounding member 71. Then, with the clamping portions 57*a*, 57*b* which protrude rearwardly of the front side surrounding member 71 inserted into the terminal holes 275 in the rear side surrounding member 271, the front end face 273 of the rear side surrounding member 271 abuts the rear end face 73 of the front side surrounding member 71. At this time, the protruding portion 279 formed on the front end face 273 of the rear side surrounding member 271 is fitted in the corresponding recess portions 79 formed on the rear end face 73 of the front side surrounding member 71. Following this, the rear end (the upper end in the figures) of the rear side surrounding member 271 is brought into contact with a front end (a lower end in the figures) of the sealing elastic member 101 (see FIG. 13).

Figure 16:
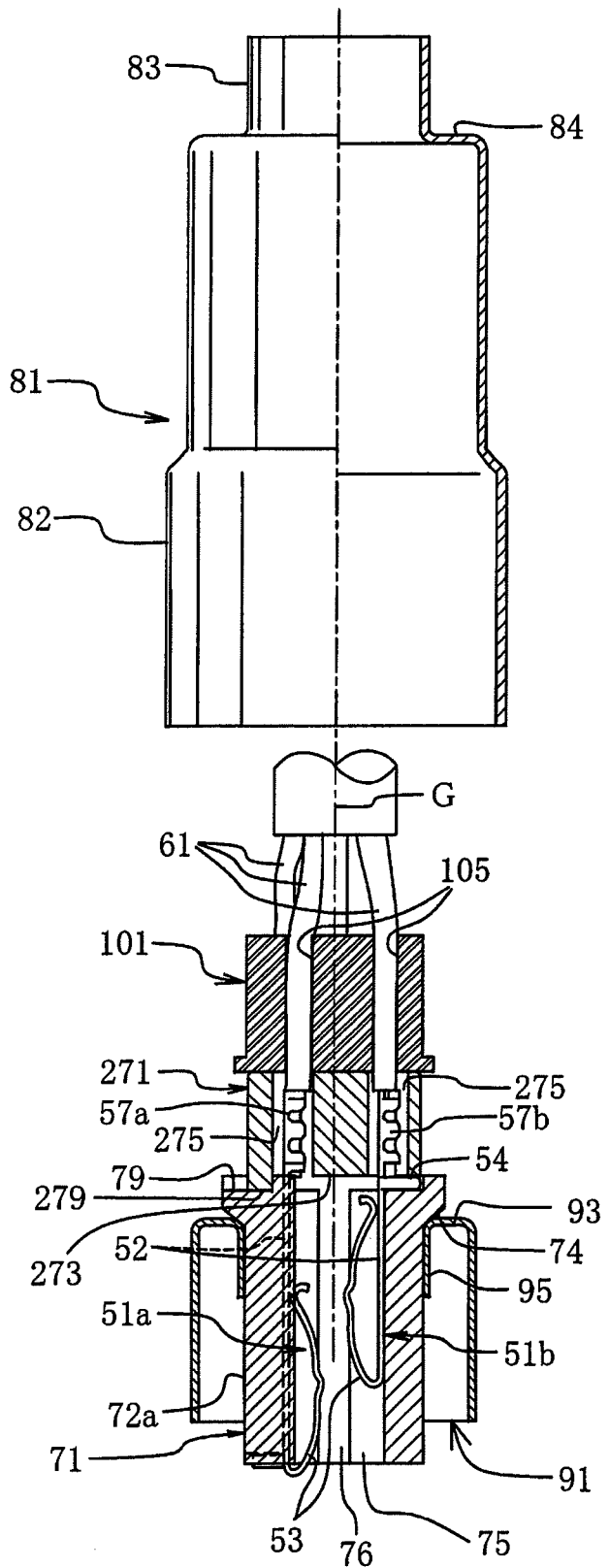
FIG. 16 is a drawing illustrating a step of fabricating the sensor of FIG. 1.

As shown in FIG. 16, the supporting member 91 is fitted on the outer circumferential surface 72*a* of the front side surrounding member 71 from a front end side (a lower side in the figure) thereof, and the rear end portion 93 of the supporting member 91 is brought into abutment with the surface of the flange 74 facing toward the front side so as to be attached thereto. Following this, the protective sleeve 81 is placed to surround the sealing elastic member 101, the rear side surrounding member 271 and the front side surrounding member 71 from the rear end side (from above in the figure). Next, with the protective sleeve 81 thus placed, the portion 85 on an outer circumferential surface of the large diameter sleeve portion 82 of the protective sleeve 81 which corresponds to an intermediate portion in the front-rear direction of the supporting member 91 is crimped so as to contract in diameter so as to be (drawn in). By this action, the terminal metal fitting side assembly half 301 shown at the top right part of FIG. 17 can be obtained.

Thereafter, axes G of both the assembly halves 201, 301 are aligned so that the rear portion 23 of the element 21 of the element side assembly half 201 is held by the terminal metal fittings 51*a*, 51*b* of the terminal metal fitting side assembly half 301 as shown in FIG. 17. Then, the assembly halves 201, 301 are made to approach each other, and the rear portion 23 of the element 21 is inserted between the facing terminal metal fittings 51*a*, 51*b*, so that their terminal connecting portions 53 are pressed against the electrode terminals 25 on the element 21. Next, a front end of the large diameter sleeve portion 82 of the protective sleeve 81 is fitted on the cylindrical portion 15 of the metal shell 11 which lies closer to the rear end thereof. Then, the fitting portion is crimped from the outer circumferential surface side and is thereafter fixed to the cylindrical portion 15 by welding. Finally, the sealing sleeve portion 83 at the rear end (the upper end in the figure) of the protective sleeve 81 is crimped so as to contract in diameter, whereby the sealing elastic member 101 is compressed in the radial direction so as to be fixed in place therein. Through this series of operations, the sensor 1 shown in FIG. 1 is obtained.

The sensor of the invention is not limited to the above embodiment, and can be modified as needed. In the sensor 1 of the embodiment, the protruding piece portions 54 are provided only on the terminal metal fittings 51*b*, which constitute part of the terminal metal fittings provided in the sensor 1, so as to be held between the rear end face 73 of the front side surrounding member 71 and the front end face 273 of the rear side surrounding member 271. However, the invention is not limited thereto. The terminal surrounding member of the invention can be embodied into terminal surrounding members having an appropriate shape and structure based on the number and shape of terminal metal fittings and lead wires. Further, in the embodiment, while the invention is embodied as a gas sensor, the sensor of the invention can also be embodied as another type of sensor such as a temperature sensor.

This application is based on Japanese Patent Application No. 2008-313928 filed Dec. 10, 2008 and Japanese Patent Application No. 2009-068460 filed on Mar. 19, 2009, the above applications incorporated herein by reference in their entirety.

What is claimed is:

1. A sensor extending in an axial direction from a front end thereof to a rear end thereof, said sensor comprising:
    a sensor element extending in the axial direction and comprising a plurality of electrode terminals;
    a plurality of terminal metal fittings pressed against and connected to respective electrode terminals of the sensor element;
    a terminal surrounding member made of an insulating material and having terminal holes in which the respective terminal metal fittings extend in the axial direction, so as to surround the plurality of terminal metal fittings; and
    a plurality of lead wires connected to the respective terminal metal fittings and which are led out from the rear end of the sensor to an outside thereof,
    wherein the terminal surrounding member is divided into a front side surrounding member and a rear side surrounding member in the axial direction, and a rear end face of the front side surrounding member abuts a front end face of the rear side surrounding member, and
    wherein the sensor comprises a fitting structure comprising a recess portion formed on one of the rear end face and the front end face and a protruding portion formed on the other of the rear end face and the front end face and fitted in the recess portion, in a state in which the rear end face of the front side surrounding member and the front end face of the rear side surrounding member abut each other, so as to prevent one of the front side surrounding member and the rear side surrounding member from rotating relative to the other of the front side surrounding member and the rear side surrounding member about an axis of the sensor, and so as to prevent one of the front side surrounding member and the rear side surrounding member from deviating in a direction perpendicular to the axis of the sensor relative to the other.

2. The sensor according to claim 1,
    wherein one or more recess portions recessed towards a front end side or one or more protruding portions protruding towards a rear end side are formed on the rear end face of the front side surrounding member, and one or more protruding portions protruding towards the front end side or one or more recess portions recessed towards the rear end side are formed on the front end face of the rear side surrounding member.

3. The sensor according to claim 2,
    wherein a plurality of recess portions recessed towards the front end side or a plurality of protruding portions protruding towards the rear end side are formed on the rear end face of the front side surrounding member, and a plurality of protruding portions protruding towards the front end side or a plurality of recess portions recessed towards the rear end side are formed on the front end face of the rear side surrounding member.

4. The sensor according to claim 3,
    wherein the protruding portions and the recess portions are formed so as to be exposed on an outer circumferential surface of the front side surrounding member and the rear side surrounding member.

5. The sensor according to claim 2,
    wherein one recess portion recessed towards the front end side or one protruding portion protruding towards the rear end side is formed on the rear end face of the front side surrounding member, and one protruding portion protruding towards the front end side or one recess portion recessed towards the rear end side is formed on the front end face of the rear side surrounding member,
    wherein the protruding portion and the recess portion are formed so as to be exposed on an outer circumferential surface of the front side surrounding member and the rear side surrounding member, and
    wherein the protruding portion and the recess portion have a shape that narrows from an outer circumferential side of the front side surrounding member and the rear side surrounding member towards a center side of the front side surrounding member and the rear side surrounding member.

6. The sensor according to claim 2,
    wherein one recess portion recessed towards the front end side or one protruding portion protruding towards the rear end side is formed on the rear end face of the front side surrounding member, and one protruding portion protruding towards the front end side or one recess portion recessed towards the rear end side is formed on the front end face of the rear side surrounding member, wherein the protruding portion and the recess portion are formed so as not to be exposed on an outer circumferential surface of the front side surrounding member and the rear side surrounding member, and wherein the protruding portion and the recess portion have an elliptical or polygonal shape when viewed in the front-rear direction.

* * * * *